US010752905B2

(12) United States Patent
Ekker et al.

(10) Patent No.: US 10,752,905 B2
(45) Date of Patent: Aug. 25, 2020

(54) METHODS AND MATERIALS FOR ASSEMBLING NUCLEIC ACID CONSTRUCTS

(71) Applicant: MAYO FOUNDATION FOR MEDICAL EDUCATION AND RESEARCH, Rochester, MN (US)

(72) Inventors: Stephen C. Ekker, Rochester, MN (US); Karl J. Clark, Rochester, MN (US); Jarryd M. Campbell, Rochester, MN (US); Chun Hang Alvin Ma, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 15/544,752

(22) PCT Filed: Jan. 20, 2016

(86) PCT No.: PCT/US2016/014014

§ 371 (c)(1),
(2) Date: Jul. 19, 2017

(87) PCT Pub. No.: WO2016/118560

PCT Pub. Date: Jul. 28, 2016

(65) Prior Publication Data

US 2018/0002707 A1 Jan. 4, 2018

Related U.S. Application Data

(60) Provisional application No. 62/105,575, filed on Jan. 20, 2015.

(51) Int. Cl.

*C07H 21/04* (2006.01)
*C12N 15/66* (2006.01)
*C12N 9/22* (2006.01)
*C12N 15/64* (2006.01)
*C12N 15/10* (2006.01)

(52) U.S. Cl.

CPC ............... *C12N 15/66* (2013.01); *C12N 9/22* (2013.01); *C12N 15/102* (2013.01); *C12N 15/1027* (2013.01); *C12N 15/1031* (2013.01); *C12N 15/64* (2013.01); *C07K 2319/00* (2013.01); *C07K 2319/80* (2013.01)

(58) Field of Classification Search

CPC ...................................................... C12N 15/66
See application file for complete search history.

(56) References Cited

U.S. PATENT DOCUMENTS

| | | | | |
|---|---|---|---|---|
| 8,748,134 B2 | 6/2014 | Zhao et al. | .................. | 435/91.2 |
| 2011/0145940 A1 | 6/2011 | Voytas et al. | ................... | 800/13 |
| 2012/0178131 A1 | 7/2012 | Voytas et al. | ............. | 435/91.52 |
| 2014/0309145 A1 | 10/2014 | Valton et al. | ................... | 506/26 |

OTHER PUBLICATIONS

Bae, et al., "Microhomology-Based Choice of Cas9 Nuclease Target Sites." *Nature Methods*, 11:705 (2014).
Bedell, et al., "In Vivo Genome Editing Using a High-Efficiency Talen System." *Nature*, 491(7422):114-118 (2012).
Boch, et al., "Breaking the Code of DNA Binding Specificity of TAL-Type III Effectors." *Science*, 326(5959):1509-1512 (2009).
Briggs, et al., "Iterative Capped Assembly: Rapid and Scalable Synthesis of Repeat-Module DNA Such as TAL Effectors from Individual Monomers." *Nucleic Acids Res*, 40(15):e117 (2012).
Campbell, et al., "Gender-Heterogeneous Working Groups Produce Higher Quality Science." *PLoS One*, 8(10):e79147 (2013a).
Campbell, et al., "New and Talented Genome Engineering Toolbox." *Circulation Research*, 113(5):571-587 (2013b).
Cermak, et al., "Efficient Design and Assembly of Custom TALEN and Other TAL Effector-Based Constructs for DNA Targeting." *Nucleic Acids Res*, 39(12):e82 (2011).
Cong, et al., "Comprehensive Interrogation of Natural Tale DNA-Binding Modules and Transcriptional Repressor Domains." *Nat Connnun*, 3:968 (2012).
Crocker, et al., "Low Affinity Binding Site Clusters Confer Hox Specificity and Regulatory Robustness." *Cell*, 160(0):191-203 (2015).
Ding, et al., "A Talen Genome-Editing System for Generating Human Stem Cell-Based Disease Models." *Cell Stern Cell*, 12(2):238-251 (2013).
Leung, et al., "Characterization of Expanded Intermediate Cell Mass in Zebrafish Chordin Morphant Embryos." *Dev Biol*, 277(1):235-254 (2005).
Liang, et al., "Fairytale: A High-Throughput TAL Effector Synthesis Platform." *ACS Synthetic Biology*, 3(2):67-73 (2014).
Ma, et al., "High Efficiency in Vivo Genome Engineering with a Simplified 15-Rvd Goldytalen Design." *PLoS One*, 8(5):e65259 (2013).
Maeder, et al., "Targeted DNA Demethylation and Activation of Endogenous Genes Using Programmable Tale-Tetl Fusion Proteins." *Nat Biotechnol*, 31(12):1137-1142 (2013).
Meeker, et al., "Method for Isolation of PCR-Ready Genomic DNA from Zebrafish Tissues." *Biotechniques*, 43(5):610, 612, 614 (2007).
Mendenhall, et al., "Locus-Specific Editing of Histone Modifications at Endogenous Enhancers." *Nat Biotechnol*, 31(12):1133-1136 (2013).
Moscou and Bogdanove "A Simple Cipher Governs DNA Recognition by TAL Effectors." *Science*, 326(5959):1501 (2009).
Nakade, et al., "Microhomology-Mediated End-Joining-Dependent Integration of Donor DNA in Cells and Animals Using Talens and CRISPR/CAS9." *Nat Commun*, 5:5560 (2014).
Neff, et al., "Mojo Hand, a Talen Design Tool for Genome Editing Applications." *BMC Bioinformatics*, 14(1):1 (2013).

(Continued)

*Primary Examiner* — Kimberly Chong
(74) *Attorney, Agent, or Firm* — Medlen & Carroll, LLP

(57) ABSTRACT

This document provides methods and materials for assembling nucleic acid constructs (e.g., TALENs). For example, methods for assembling TALEs that are rapid, flexible for use in many cloning scaffolds (such as common nuclease and nickase backbones), and achievable with standard molecular biology laboratory tools, thereby making TALEs a more accessible genome system, are provided.

15 Claims, 5 Drawing Sheets

Specification includes a Sequence Listing.

(56) References Cited

OTHER PUBLICATIONS

Reyon, et al., "Flash Assembly of Talens for High-Throughput Genome Editing." *Nat Biotechnol*, 30(5):460-465 (2012).
Sakuma, et al., "Efficient Talen Construction and Evaluation Methods for Human Cell and Animal Applications." *Genes Cells*, 18(4):315-326 (2013).
Sanjana, et al., "A Transcription Activator-Like Effector Toolbox for Genome Engineering." *Nat Protoc*, 7(1):171-192 (2012).
Schmid-Burgk, et al., "A Ligation-Independent Cloning Technique for High-Throughput Assembly of Transcription Activator-Like Effector Genes." *Nat Biotechnol*, 31(1):76-81 (2013).
Schulte-Merker, et al., "The Zebrafish Organizer Requires Chordino." *Nature*, 387(6636):862-863 (1997).
Thanisch, et al., "Targeting and Tracing of Specific DNA Sequences with dTALES in Living Cells." *Nucleic Acids Research*, 42(6):e38-e38 (2014).
Uhde-Stone, et al., "A Do-It-Yourself Protocol for Simple Transcription Activator-Like Effector Assembly." *Biological Procedures Online*, 15(1):3 (2013).
Wang, et al., "Reprogramming the Genetic Code: From Triplet to Quadruplet Codes." *Angew Chem Int Ed Engl*, 51(10):2288-2297 (2012).
Yu and McVey "Synthesis-Dependent Microhomology-Mediated End Joining Accounts for Multiple Types of Repair Junctions." *Nucleic Acids Research*, 38(17):5706-5717 (2010).

A
pXX-1 plasmids each carrying one of the 4 possible RVDs
pHD-1
pNG-1
pNI-1
pNN-1
pXX-M or -MM plasmids each carrying one of the 4 possible RVDs
pHD-M
pNG-M
pNI-M
pNN-M
pXX-10 plasmids each carrying one of the 4 possible RVDs
pHD-10
pNG-10
pNI-10
pNN-10
Library destination vectors: pFusX1 – pFusX4
pFusX #
B
pHD-1
+
pNN-M
+
pHD-10
+
pFusX1
pFusX1-HD-NN-HD
1 of 64 possible combinations A
B
C
D
pFusX kit
GGT Kit
% of somatic NHEJ
p=0.63
p=0.65
p=0.50
FLT3 P1
FLT3 P2
FLT3 P3
TALEN ID#
Exon-1
ATG
CHD P1
Wild-type
chd MO
CHD P1
i
ii
iii 3
2
1
4
FusX plate
A B C D E F G H
X1
X2
X3
T
B2
+
B3
M
X4
R
Q
A
B
C
D

METHODS AND MATERIALS FOR ASSEMBLING NUCLEIC ACID CONSTRUCTS

This application claims priority to U.S. provisional Application Ser. No. 62/105,575, filed on Jan. 20, 2015, which is herein incorporated by reference.

This invention was made with government support under GM063904 and DK084567 awarded by the National Institutes of Health. The government has certain rights in the invention.

TECHNICAL FIELD

This document relates to methods and materials for assembling nucleic acid constructs. For example, this document provides methods and materials for assembling transcription activator-like effector nucleases (TALENs).

BACKGROUND INFORMATION

Transcription activator-like effectors (TALEs) are important genome science tools (see, e.g., Campbell et al., *Circ. Res.,* 113:571-587 (2013); U.S. Pat. No. 8,748,134 issued on Jun. 10, 2014; U.S. Pat. Publication No. US 2011/0145940; Cermak et al., Nucleic Acids Res. 2011 July; 39(12):e82. doi: 10.1093/nar/gkr218), including an array of applications from locus-specific DNA editing, artificial transcriptional activators and repressors, locus-specific epigenetic modification, or live subcellular imaging. TALEs as nucleases (TALENs) are popular genome editing tools that are extensively deployed in both in vitro cell systems and diverse model organisms. Native to the plant pathogen *Xanthomonas*, TALEs normally function as transcription factors. TALEs were harnessed in molecular biology applications to target almost any DNA sequence and effect changes to nearby DNA and genes when fused to other proteins such as endonucleases or activator and repressor domains. The DNA recognition sequence of the TALE is typically a repetitive tract encoding 33-35 amino acid residues, with the last repetitive module being a partial or half (20 amino acids) length. Two variable, adjacent positions, 12 and 13, within this repetitive sequence (known as repeat-variable di-residues, or RVDs) are responsible for distinguishing between the four DNA nucleotides (Moscou and Bogdanove, *Science,* 326:1501-1508 (2009); and Boch et al., *Science,* 326:1509-1512 (2009)). Commonly used RVDs, each preferentially targeting a specific nucleotide, include: NI, NN=adenine; HD=cytosine; NK, NN, NH=guanine, NG=thymine.

By fusing multiple RVD modules in a specific order, a TALE can be targeted to a corresponding linear DNA sequence. Diverse protocols have been developed to efficiently assemble these repeat modules. The Golden Gate TALE system (Golden Gate TALEN and TAL Effector Kit 2.0, referred to herein as GGT Kit) is a popular assembly method (Cermak, et al., *Nucleic Acids Res.,* 39:e82 (2011)). This is a 3-step, 5-day Golden Gate assembly process deployed in many laboratories thanks in part to its flexibility, low start-up cost, and requirement of small number of common molecular cloning reagents. Several high throughput TALEN assembly methods (Reyon et al., *Nat. Biotechnol.,* 30:460-465 (2012); Briggs et al., *Nucleic Acids Res.,* 40:e117 (2012); Wang et al., *Angew. Chem. Int. Ed. Engl.,* 51:8505-8508 (2012); Sanjana et al., *Nat. Protoc,* 7:171-192 (2012); Schmid-Burgk et al., *Nat. Biotechnol.,* 31:76-81 (2012); Sakuma et al., *Genes Cells,* 18:315-326 (2013); Uhde-Stone et al., *Biol. Proced. Online,* 15:3 (2013); and Ding et al., *Cell Stem Cell,* 12:238-251 (2013)) offer unique advantages over the GGT kit and include features like automation, but each of these systems also come with specific limitations. For example, the lowest supply cost assembly system reported to date requires the purchase of a liquid handling robot (Liang et al., *ACS Synth. Biol,* 3:67-73 (2014)).

SUMMARY

In one embodiment, the invention provides a method for assembling a polynucleotide sequence that encodes a transcription activator-like effector (TALE)-DNA modifying enzyme that comprises (A) a TALE binding domain comprising a plurality of repeat modules, and (B) a DNA modifying enzyme domain, wherein the method comprises combining, in a single reaction mixture, (a) a plurality of DNA segments, wherein an individual DNA segment of the plurality of DNA segments encodes a repeat module of the TALE binding domain repeat modules, and wherein the plurality of DNA segments comprises at least two trimer DNA sequences, and (b) a first expression vector encoding the DNA modifying enzyme domain wherein the combining is under conditions so as to generate a second expression vector encoding the polynucleotide sequence encoding the TALE-DNA modifying enzyme in a single cloning reaction.

In one preferred embodiment, the TALE binding domain comprises n repeat modules, wherein n is an integer, and the reaction mixture comprises from two of the trimer DNA sequences to n/3 trimer DNA sequences. In a further embodiment, the reaction mixture comprises n/3 trimer DNA sequences. In yet another embodiment, the reaction mixture comprises (n−1)/3 trimer DNA sequences. In another embodiment, the reaction mixture comprises (n−2)/3 trimer DNA sequences. In a further embodiment, the reaction mixture comprises (n−3)/4 trimer DNA sequences. In a particular embodiment, the TALE binding domain further comprises a portion of a repeat module that is operably linked at the C-terminal end of the plurality of repeat modules, and wherein the method further comprises combining, in the single reaction mixture, a DNA sequence encoding the portion of a repeat module. In one embodiment, the DNA sequence encoding the portion of a repeat module is comprised in an expression vector. In another preferred embodiment, each trimer DNA sequence of the at least two trimer DNA sequences is comprised in an expression vector. In another embodiment, the single reaction mixture further comprises one or more restriction enzymes and one or more DNA ligases. In yet a further embodiment, the method further comprises purifying the generated polynucleotide sequence encoding the TALE-DNA modifying enzyme. In one embodiment, the method is automated.

The invention also provides a kit comprising a first plurality of wells that contain sixty four (64) trimer repeat modules of a TALE binding domain, wherein each of the plurality of wells contains one trimer repeat module of the 64 trimer repeat modules. In a particular embodiment, the kit further comprises a second plurality of wells that contain a portion of a repeat module of a TALE binding domain. In a further embodiment, the kit further comprises a third plurality of wells that contain an expression vector encoding a DNA modifying enzyme domain. In one preferred embodiment, the first plurality of wells, the second plurality of wells, and the third plurality are comprised on the same plate or on different plates. In a particular embodiment, the number of wells of the plurality of wells is 96.

BRIEF DESCRIPTION OF THE INVENTION

This document provides methods and materials for assembling nucleic acid constructs (e.g., TALENs). For example, this document provides methods for assembling TALEs that are rapid, flexible for use in many cloning scaffolds (such as common nuclease and nickase backbones), and achievable with standard molecular biology laboratory tools, thereby making TALEs a more accessible genome system. In some cases, the methods provided herein can be single-tube modified assembly methods (referred to herein as FusX) that are fully backward compatible with the GGT Kit with a 3-day optimal completion time. As described herein, over 160 TALE arrays were successfully assembled using this FusX protocol, with over 90% of these TALEs successfully assembled in the first pass. Twenty seven pairs were quantitatively tested for activity using the zebrafish gene targeting system, each showing high somatic and germline activity, with many TALENs showing bi-allelic somatic targeting rates. Through a better understanding of the cell's endogenous DNA repair mechanisms, one can improve reagent design and targeting to achieve predictable outcomes. Microhomology mediated end joining (MMEJ) appears to be a dominant repair pathway for TALEN-induced double-strand breaks and was used to generate predictable deletions or to incorporate donor DNA sequences in a highly efficient manner (Bae et al., *Nat. Methods,* 11:705-706 (2014); and Nakade et al., *Nat. Commun.,* 5:5560 (2014)). Several loci presented here, including the chordin locus, confirmed the usefulness of microhomology prediction analyses. Once established, the FusX system is comparable in assembly time and reagent cost to other custom genomic tools, while offering high activity and unparalleled specificity and genomic targeting flexibility. These features can be important for the time-sensitive assessment of gene function for personalized medicine applications.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DEFINITIONS

Figure 1:
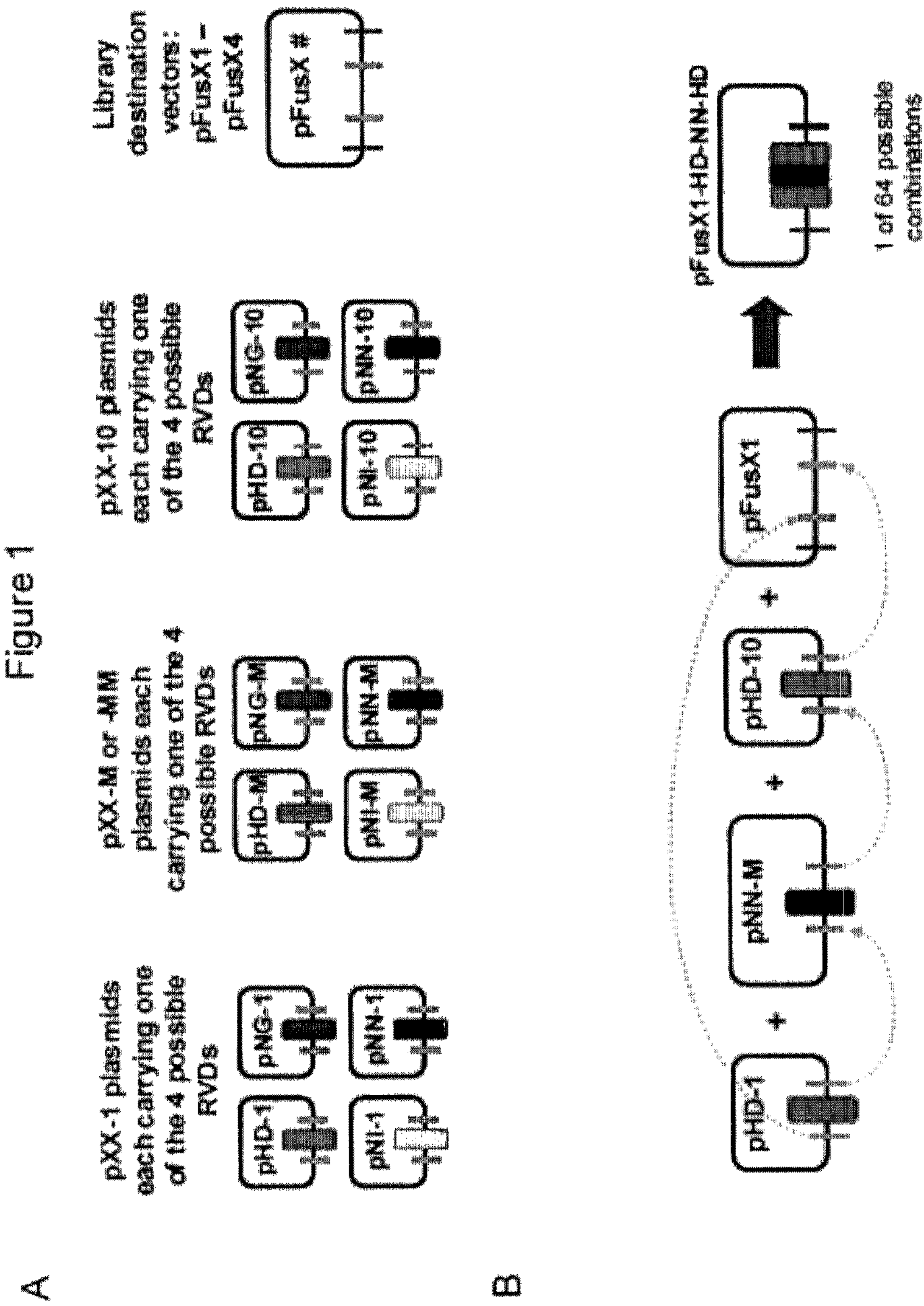
FIG. 1. Construction of pFusX1-4 libraries. A) Components plasmids used to construct pFusX1-4 libraries. pXX-1 and pXX-10 are single-RVD carrying plasmid from the original Golden Gate system (2.0) (Cermak et al., *Nucleic Acids Res.,* 39:e82 (2011)); pXX-M and -MM are new single RVD module with designated sequence and 5' and 3' BsaI overhangs for ligation in between pXX-1 and pXX-10 to form 3-mer intermediates in pFusX1-4 libraries. pXX-MM carry extra silent mutations and is only used to construct pFusX3 library, providing a specific primer binding site for sequencing of long TALE domain. "XX" represents any of the 4 RVD modules: HD, NG, NI, NN. B) Schematic diagram showing sequential ligation of single RVD component plasmids into the 4 intermediate vectors: pFusX1, pFusX2, pFusX3, pFusX4. Dotted arrows indicate ligation at compatible overhangs generated by BsaI.

To facilitate understanding of the invention, a number of terms are defined below.

"Transcription activator-like effector (TALE)-DNA modifying enzyme" refers to a protein comprising a "Transcription Activator-Like effector (TALE) binding domain" and a "DNA-modifying enzyme domain."

"DNA modifying enzyme domain" refers to any protein which modifies the genetic material of a cell (e.g., DNA and/or RNA), such as by cleavage, covalent interaction, water-mediated interaction, etc. DNA modifying enzyme is exemplified by nuclease, methylase, topoisomerase, integrase, transposase, ligase, transcription activators or repressor, histones, etc. When comprised in a TALE-DNA modifying enzyme the DNA modifying enzyme is referred as the DNA modifying enzyme domain.

"Nuclease" and "restriction enzyme" interchangeably refer to any wild-type or variant enzyme capable of catalyzing the hydrolysis (cleavage) of bonds between nucleic acids within a DNA or RNA molecule, preferably a DNA molecule. Nuclease includes exonuclease and endonuclease. Non-limiting examples of endonucleases are described in Voytas et al., U.S. Pat. Appl. No. 20440445940, and include type II restriction endonucleases such as FokI, HhaI, HindIII, Nod, BbvCI, EcoRI, BglI, and AlwI. Endonucleases comprise also rare-cutting endonucleases when having typically a polynucleotide recognition site of about 42-45 base pairs (bp) in length, more preferably of 44-45 bp. Rare-cutting endonucleases significantly increase HR by inducing DNA double-strand breaks (DSBs) at a defined locus. Rare-cutting endonucleases can for example be a homing endonuclease, a chimeric Zinc-Finger nuclease (ZFN) resulting from the fusion of engineered zinc-finger domains with the catalytic domain of a restriction enzyme such as FokI, and/or a chemical endonuclease. In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences. Examples of such endonuclease that are within the scope of the invention include I-Sce I, I-Chu I, I-Cre I I-Csm I PI-Sce I, PI-Tli I, PI-Mtu I I-Ceu I I-Sce II, I-Sce III, HO, PI-Civ I PI-Ctr I, PI-Aae I PI-Bsu I PI-Dha I PI-Dra I, PI-Mav I, PI-Mch I PI-Mfu I, PI-Mfl I PI-Mga I, PI-Mgo I PI-Min I, PI-Mka I, PI-Mle I PI-Mma I, PI-Msh I, PI-Msm I PI-Mth I PI-Mtu I PI-Mxe I PI-Npu I PI-Pfu I, PI-Rma I PI-Spb I PI-Ssp I, PI-Fac I, PI-Mja I PI-Pho I, PI-Tag I, PI-Thy I, PI-Tko I PI-Tsp I I-MsoI.

"Ligase" refers to an enzyme that catalyzes the joining of two nucleotide sequences (e.g., DNA and/or RNA) by catalyzing the formation of a phosphodiester bond. DNA ligases used in molecular biology to insert DNA fragments into expression vectors (e.g., plasmids) are exemplified by T4 DNA ligase.

"Transcription activator-like effector nuclease" ("TALEN") refers to a recombinant protein comprising a "Transcription Activator-like effector (TALE) binding domain" and an endonuclease domain. In other words, "TALEN" refers to a transcription activator-like effector (TALE)-DNA modifying enzyme in which the DNA modifying enzyme is a nuclease.

"Transcription Activator-Like effector (TALE) binding domain" refers to a protein that contains a "repeat region" (also referred to as "repeat domain"), which contains a plurality of repeated highly conserved 33-34 amino acid sequence (referred to as a "repetitive module" and "repeat module"), with the last repetitive module at the C-terminal end being a partial or half (approximately 20 amino acids) length. The combination of repetitive modules in the repeat region binds to a specific nucleotide sequence in the target DNA and/or RNA sequence, such that the (TALE)-DNA modifying enzyme modifies the target DNA and/or RNA within or adjacent to the specific nucleotide sequence in the cell or progeny thereof. The repetitive modules of the repeat region have divergent 12th and 13th amino acids. These 12th and 13th amino acid positions (referred to as the "Repeat Variable Diresidue," "RVD," and "RVD module") are highly variable and show a strong correlation with specific nucleotide recognition. This straightforward relationship between amino acid sequence of the RVD and target DNA recognition has allowed for the engineering of specific DNA-binding domains by selecting a combination of repeat segments containing the appropriate RVDs. By fusing multiple RVD modules in a specific order, a TALEN can be targeted to a corresponding linear DNA sequence. RVDs each preferentially targeting a specific nucleotide are known in the art (e.g., Zhao et al., U.S. Pat. No. 8,748,134; Voytas et al., U.S. Pat. Appl. No. 20440445940), and are exemplified by: NI, NN=adenine; HD=cytosine; NK, NN, NH=guanine, NG=thymine (see Voytas et al., U.S. Pat. Appl. No. 20440445940). Prior art recombinant synthesis of TALE-DNA modifying enzymes (such as TALEN) has been problematic because of improper annealing of the repetitive sequence found in the TALE binding domain. Functional TALENs may be monomeric or dimeric. A "monomeric" TALEN contains one Transcription Activator-like effector (TALE) binding domain fused to one endonuclease domain. A "dimeric" TALEN results from the fusion of two monomeric TALENs. The dimerization can result in a "homodimeric" TALEN when both monomeric TALEN are identical, or can result in a "heterodimeric" TALEN when monomeric TALEN are different. Two monomeric TALEN are different when, for example, their RVDs numbers are different, and/or when the content (i.e., amino acid sequence) of at least one RVD is different.

"Portion" and "fragment" when made in reference to a nucleic acid sequence or protein sequence refer to a piece of that sequence that may range in size from two (2) contiguous nucleotides and amino acids, respectively, to the entire sequence minus one nucleotide and amino acid, respectively. For example, a portion of a 34-amino acid sequence (such as a repetitive module sequences of a Transcription Activator-Like effector (TALE) binding domain) refers to a sequence that ranges in size from any numerical value from 2 to 33 contiguous amino acids, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, and/or 33 amino acids.

"At least a portion of" a nucleic acid sequence or protein sequence refers to a piece of that sequence that may range in size from two (2) contiguous nucleotides and amino acids, respectively, to the entire sequence. For example, at least a portion of ?

"Plurality," "multiple," and grammatical equivalents mean 2 (two) or more. For example, multiple trimer DNA sequences refers to two or more trimer sequences, such as any ranges of numbers from 2 to 200, including any ranges of numbers from 5 to 20, including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc. of trimer DNA sequences. In one preferred embodiment, multiple trimer DNA sequences refers to any ranges of numbers from 5 to 20. In another example, a plurality of DNA segments refers to two or more DNA segments, such as any ranges of numbers from 2 to 200, including any ranges of numbers from 5 to 20, including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50, etc. of DNA segments. In one preferred embodiment, a plurality of DNA segments refers to any ranges of numbers from 5 to 20.

"Trimer" and "triple" when in reference to a DNA sequence, interchangeably refer to a nucleotide sequence of three operably linked DNA sequences. For example, a "trimer" repeat module of a TALE binding domain refers to three operably linked repeat modules, and is represented by one of the 64 possible combinations of repeat modules that preferentially target an adenine, cytosine, guanine, or thymine.

The term "expression vector" as used herein refers to a nucleotide sequence containing a desired coding sequence and appropriate nucleic acid sequences necessary for the expression (i.e., transcription into RNA and/or translation into a polypeptide) of the operably linked coding sequence in a particular host cell. Expression vectors are exemplified by, but not limited to, plasmid, phagemid, shuttle vector, cosmid, virus, chromosome, mitochondrial DNA, plastid DNA, and nucleic acid fragments thereof. Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals. Expression vectors include "gene therapy viral vectors," viral vectors comprising a therapeutic nucleotide sequence.

"Backbone vector" and "receiver vector" interchangeably refer to an expression vector that contains a polynucleotide encoding a DNA modifying enzyme domain, such as a nuclease. Thus, a "TALEN backbone" vector refers to an expression vector that contains a polynucleotide encoding a nuclease.

"Automated" means operated and/or controlled by a mechanical device (e.g., robot) and/or an electronic device (e.g., computer), preferably without continuous input from a human operator.

"Purify" and grammatical equivalents thereof when in reference to a desirable component (such as cell, protein, nucleic acid sequence, carbohydrate, glycoprotein, etc.) refer to the reduction in the amount of at least one undesirable component (such as cell, protein, nucleic acid sequence, carbohydrate, glycoprotein etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in "enrichment" (i.e., an increase) in the amount of the desirable component relative to one or more undesirable component. For example, polynucleotides encoding TALENs may be purified by removing incomplete ligation products (e.g., linear DNA segments) using a plasmid-safe Deoxyribonuclease (DNase). (Zhao et al., U.S. Pat. No. 8,748,134).

DETAILED DESCRIPTION AND EXAMPLES

Example 1—FusX: A Rapid One-Step Golden Gate TALE Assembly System for Genome Science Generating the FusX TALE Assembly System Modification of Tandem TALE Intermediate Assembly Vectors: pFusX1-pFusX4

No modifications were required to generate pFusX1, which is the same as the original GGT kit assembly vector, pFus_A30A. The assembly vectors, pFusX2, pFusX3 and pFusX4 (X2, X3 and X4) were modified from pFus_A30B of the original GGT kit (Cermak et al., *Nucleic Acids Res.,* 39:e82 (2011)). Modifications to pFusA_30B were made via removal of a small fragment using different restriction endonuclease combinations for each assembly vector X2, X3 or X4. These sequence fragments were replaced with modified short oligonucleotides to generate specific four-base overhangs upon BsmBI digestion (Table 1 and 2). The nature of the specific BsmBI overhangs allows the pFusX components to be assembled in tandem into the final TALE array (FIG. 1). For pFusX2, the replacement oligonucleotide fragment was produced by self-annealing oligonucleotides; for pFusX3 and pFusX4, the fragment was generated by PCR (Table 1). All four pFusX (X1-X4) vectors were available from Addgene.

TABLE 1

Modification of TALE intermediate vectors. Restriction enzymes and sequences of short oligos or primers used in cloning for modification of pFus_A30B into pFusX2, pFusX3 and pFusX4. For pFusX2, annealed reverse complementary short oligos are used directly as insert. For pFusX3 and pFusX4, PCR products from primers with pFus_A30B as template are used as inserts. No modification is needed for pFusX1, which is identical to pFus A30B.

| Vector | Backbone | Insert type | Subcloning enzymes | SEQ ID NOS: | Sequence of short oligos or PCR primers |
|---|---|---|---|---|---|
| pFusX1* | pFus_A30A | N/A | N/A | 1, 2 | N/A |
| pFusX2 | pFus_A30B | short oligos | AgeI/AatII | | pFusX-S: CCGGTGGTCTCTGGCGGCAAGCAAGCGCTCGAAACGGTGCAGCGGCTGTTGCCGGTGCTGTGCCAGGACCATGGCGAGACGT<br>pFusX2-AS: CTCGCCATGGTCCTGGCACAGCACCGGCAACAGCCGCTGCACCGTTTCGAGCGCTTGCTTGCCGCCAGAGACCA |
| pFusX3 | pFus_A30B | PCR** | AflII/AatII | 3, 4 | pFusX3-F: ATTCTTAAGCGTCTCCATGGCCTGACCCCG<br>pFusX3-R: ATTGACGTCTCGCAGGCCATGGTCCTGG |
| pFusX4 | pFus_A30B | PCR** | AflII/AatII | 5, 6 | pFusX4-F: GTTCTTAAGCGTCTCCCCTGACCCCG<br>pFusX4-R: GTTGACGTCTCGGCCATGGTCCTGG |

*no modification is required for pFusX1

**PCR template: pFus_A30B

TABLE 2

FusX system libraries required for making 15, 16 and 17-mer TALEs. Detail information including library names, plasmid quantities, description, 5' and 3' overhangs sequences produced by BsmBI digestion of the 9 plasmid libraries required for making 15, 16 and 17-mer TALEs. Compatible overhangs of destination vector with pFusX1 and pLR are highlighted in Blue and Red, respectively.

| Library name | No. of plasmids | Description | SEQ ID NOS: | BsmBI 5' over-hang | SEQ ID NOS: | BsmBI 3' over-hang |
|---|---|---|---|---|---|---|
| pFusX1 | 64 | All 3-RVD modules occupying positions 1-3 in full-length TALE domain | 7, 8 | 5' CGTCTCC **CCCT** 3'<br>3' GCA-GAGGGGGA 5' | 9, 10 | 3' GCAGAGCA-GTC 5'<br>5' CGTCTCG **TCAG** 3' |
| pFusX2 | 64 | All 3-RVD modules occupying positions 4-6 in full-length TALE domain | 11, 12 | 5' CGTCTCC **CTGA** 3'<br>3' GCA-GAGGGACT 5' | 13, 14 | 3' GCAGAGCG-GTA 5'<br>5' CGTCTCG **CCAT** 3' |
| pFusX3 | 64 | All 3-RVD modules occupying positions 7-9 in full-length TALE domain | 15, 16 | 5' CGTCTCC **ATGG** 3'<br>3' GCAGAGG-TACC 5' | 17, 18 | 3' GCA-GAGCGTCC 5'<br>5' CGTCTCG **CAGG** 3' |
| pFusX4 | 64 | All 3-RVD modules occupying positions 10-12 in full-length TALE domain | 19, 20 | 5' CGTCTCC **CCTG** 3'<br>3' GCA-GAGGGGAC 5' | 21, 22 | 3' GCAGAGC-CGGT 5'<br>5' CGTCTCG **GCCA** 3' |
| pFus_B2 | 16 | All 2-RVD modules occupying positions 13-14 in full-length 15-mer TALE domain | 23, 24 | 5' CGTCTCA **TGGC** 3'<br>3' GCAGAG-TACCG 5' | 25, 26 | 3' GCAGAGC-TATC 5'<br>5' CGTCTCG **ATAG** 3' |
| pFus_B3 | 64 | All 3-RVD modules occupying positions 13-15 in full-length 16-mer TALE domain | 27, 28 | 5' CGTCTCA **TGGC** 3'<br>3' GCAGAG-TACCG 5' | 29, 30 | 3' GCAGAGC-TATC 5'<br>5' CGTCTCG **ATAG** 3' |
| pFus_B4 | 256 | All 4-RVD modules occupying positions 13-16 in full-length 17-mer TALE domain, previously described ** | 31, 32 | 5' CGTCTCA **TGGC** 3'<br>3' GCAGAG-TACCG 5' | 33, 34 | 3' GCAGAGC-TATC 5'<br>5' CGTCTCG **ATAG** 3' |
| pLR | 4 | half-repeat mod-ules for the last RVD of TALE domain, previously described *** | 35, 26 | 5' CGTCTCG **CTAT** 3'<br>3' GCAGAGC-GATA 5' | 37, 38 | 3' GCAGAGAG-CAA 5'<br>5' CGTCTCT **CGTT** 3' |
| Compatible destination vector(s) | A variety exists for different application (see Campbell et al., 2013) | With the remaining TALEN sequence and compatible BsmBI overhangs* for insertion of RVD modules | 39, 40 | 5' CGTCTCC **AGGG** 3'<br>3' GCAGAG-GTCCC 5' | 41, 42 | 3' GCAGAGGT-TGC 5'<br>5' CGTCTCC **AACC** 3' |

*Compatible overhangs of destination vector with pFusX1 and pLR are highlighted in Blue (larger font) and Red (smaller font), respectively.

**Liang et al., ACS Synth. Biol., 3:67-73 (2014).

***Moscou and Bogdanove, Science, 326:1501 (2009).

Synthesis of "Middle" TALE Repeat Monomers: pXX-M and pXX-MM

Each pFusX1-X4 assembly vector was used to make intermediate libraries of every possible combination of 3 TALE repeat monomers (RVDs: NI, HD, NN and NG). As there are four possible RVDs and three possible positions, there are $4^3$=64 combinations per trimer library. Because the recipient pFusX1-pFusX4 intermediate vectors were generated from the original GGT kit (either pFus_A30A or pFus_A30B vectors), they retained their original BsaI sites, used in the first Golden Gate (GG-1) reaction (Cermak, et al., *Nucleic Acids Res.,* 39:e82 (2011)). Thus, the original RVD monomers of position 1 and 10 from the GGT kit could be recycled as well, becoming the first and last RVD positions, respectively, in the pFusX1-X4 intermediate libraries. Therefore, it was necessary to generate only monomers of the middle position, having modified BsaI sites that are compatible with the 3' overhang of position 1 and the 5' overhang of position 10.

To synthesize the new, middle TALE repeat monomers (M), sense and anti-sense short oligonucleotides were designed for each RVD to produce inserts with specific 5' and 3' BsaI overhangs. For simplicity, the designation XX was used to refer to any of the four RVD monomers. The overhangs from the middle RVD monomer linked BsaI-digested inserts from pXX-1 and pXX-10 to form complete three-TALE repeat intermediates that were introduced into the pFusX1-pFusX4 vectors in the equivalent GG-1 reaction (Table 3). Another set of oligonucleotides was designed for each middle RVD monomer with silent mutations introduced into a region of the consensus repeat sequence. These modified-middle repeats (MM) were only introduced into the pFusX3 intermediate library to create a unique priming site in the full-length RVD array. All oligonucleotides were self-annealed and TA cloned into pSC-A using StrataClone PCR Cloning Kit (Agilent Technologies, Santa Clara, Calif., USA), for use in the GG-1 reaction. All middle (pSC-A-XX-M) and modified-middle (pSC-A-XX-MM) monomers were available from Addgene.

TABLE 3

Components used to build the FusX system (pFusX and pFus_B# libraries). Detail information including plasmid names, plasmid quantities, description, 5' and 3' overhangs sequences produced by Bsai digestion of all the component plasmids used to synthesize FusX system libraries. XX represents any of the 4 RVDs: HD, NG, NI, NN and compatible overhangs are highlighted with same color.

| Plasmid name* | No. of plasmids | Description | SEQ ID NOS: | BsaI 5' overhang** | SEQ ID NOS: | BsaI 3' overhang** |
|---|---|---|---|---|---|---|
| Components used to make pFusX1, pFusX2, pFusX3 and pFusX4 libraries | | | | | | |
| pXX-1 | 4 | Single-RVD modules which occupy position 1 in all 3-mer of each pFusX library, previously described *** | 43, 44 | 5' GGTCTCG**CTAT** 3' #1<br>3' CCAGAGCGATA 5' | 45, 46 | 3' CCAGAGGGTAC 5'<br>5' GGTCTCC**CATG** 3' |
| pXX-M | 4 | Single-RVD modules which occupy position 2 in all 3-mer of pFusX1, pFusX2 and pFusX4 libraries | 47, 48 | 5' GGTCTCG**CATG** 3'<br>3' CCAGAGCGTAC 5' | 49, 50 | 3' CCAGAGACTCG 5'<br>5' GGTCTCT**GAGC** 3' |
| pXX-MM | 4 | Single-RVD modules which occupy position 2 in all 3-mer of pFusX3 library with silent mutations | 51, 52 | 5' GGTCTCG**CATG** 3'<br>3' CCAGAGCGTAC 5' | 53, 54 | 3' CCAGAGACTCG 5'<br>5' GGTCTCT**GAGC** 3' |
| pXX-10 | 4 | Single-RVD modules which occupy position 3 in all 3-mer of each pFusX library, previously described *** | 55, 56 | 5' GGTCTCC**GCTC** 3'<br>3' CCAGAGCCGAG 5' | 57, 58 | 3' CCAGAGGGCGG 5'<br>5' GGTCTCC**CGCC** 3' #2 |
| pFusX1-4 | 4 | Intermediate assembly vectors used to create 3-mer libraries | 59, 60 | 5' GGTCTCG**ATAG** 3' #1<br>3' CCAGAGCTATC 5' | 61, 77 | 3' CCAGAGACCGC 5'<br>5' GGTCTCT**GGCG** 3' #2 |

TABLE 3-continued

Components used to build the FusX system (pFusX and pFus_B# libraries). Detail information including plasmid names, plasmid quantities, description, 5' and 3' overhangs sequences produced by Bsai digestion of all the component plasmids used to synthesize FusX system libraries. XX represents any of the 4 RVDs: HD, NG, NI, NN and compatible overhangs are highlighted with same color.

| Plasmid name* | No. of plasmids | Description | SEQ ID NOS: | BsaI 5' overhang** | SEQ ID NOS: | BsaI 3' overhang** |
|---|---|---|---|---|---|---|
| Components used to make pFus B2, pFus B3 and pFus B4 libraries, previously described*** | | | | | | |
| pXX-1 | 4 | Single-RVD modules which occupy position 1 in all pFus_B libraries | 43, 44 | 5' GGTCTCG**CTAT** 3' #1<br>3' CCAGAGCGATA 5' | 62, 63 | 3' CCAGAGGGTAC 5'<br>5' GGTCTCC**CATG** 3' |
| pXX-2 | 4 | Single-RVD modules which occupy position 2 in all pFus_B libraries | 64, 65 | 5' GGTCTCC**CATG** 3'<br>3' CCAGAGGGTAC 5' | 66, 67 | 3' CCAGAGCCAGG 5'<br>5' GGTCTCG**GTCC** 3' #3 |
| pXX-3 | 4 | Single-RVD modules which occupy position 3 in all pFus_B libraries | 68, 69 | 5' GGTCTCA**GGAC** 3'<br>3' CCAGAGTCCTG 5' | 70, 71 | 3' CCAGAGGGACC 5'<br>5' GGTCTCC**CTGG** 3' #4 |
| pXX-4 | 4 | Single-RVD modules which occupy position 4 in pFus B4 library | 72, 73 | 5' GGTCTCG**CCAG** 3'<br>3' CCAGAGCGGTC 5' | 74, 75 | 3' CCAGAGGTTGT 5'<br>5' GGTCTCC**AACA** 3' #5 |
| pFus_B2 | 1 | Intermediate vector used for 2-mer pFus_B2 library | 43, 60 | 5' GGTCTCG**ATAG** 3' #1<br>3' CCAGAGCTATC 5' | 76, 77 | 3' CCAGAGTCCTG 5'<br>5' GGTCTCA**GGAC** 3' #3 |
| pFus_B3 | 1 | Intermediate vector used for 3-mer pFus_B3 library | 43, 60 | 5' GGTCTCG**ATAG** 3' #1<br>3' CCAGAGCTATC 5' | 78, 79 | 3' CCAGAGCGGTC 5'<br>5' GGTCTCG**CCAG** 3 #4 |
| pFus_B4 | 1 | Intermediate vector used for 4-mer pFus_B4 library | 43, 60 | 5' GGTCTCG**ATAG** 3' #1<br>3' CCAGAGCTATC 5' | 80, 81 | 3' CCAGAGGACAA 5'<br>5' GGTCTCC**TGTT** 3' #5 |

*XX represents any of the 4 RVDs: HD, NG, NI, NN.
**Compatible overhangs are highlighted with same color and #.
***Moscou and Bogdanove, Science, 326:1501 (2009).

Synthesis of TALE Intermediate Libraries

All TALE intermediate libraries were synthesized through a mixed GG-1 reaction. For pFusX1, X2 and X4, all 12 pXX-1, pXX-M and pXX-10 were combined with a single pFusX vector. For pFusX3, pXX-MM was used instead of pXX-M and for pFus_B2 and pFus_B3, pXX-1 and pXX-2 or pXX-1, pXX-2 and pXX-3 were used, respectively (FIG. 1). Briefly for each reaction, 25 ng of each plasmid (for trimer libraries, 13 plasmids; for dimer libraries, 9 plasmids) were combined with 10 U BsaI (New England BioLabs, Ipswich, Mass., USA) and 400 U T4 DNA ligase (New England BioLabs, Ipswich, Mass., USA), in 1× T4 DNA ligase buffer (reaction volume: 20 µL). Three digest-ligation cycles were performed (10 minute digest at 37° C.; 15 minute ligation at 16° C.), followed by two 5 minute inactivation steps at 50° C. and 80° C. To each reaction 0.5 µL ATP (25 mM) and 5 U plasmid-safe DNase (Epicentre, Madison, Wis., USA) were added and incubated at 37° C. for 1 hour, followed by inactivation at 70° C. for 30 minutes. Chemically competent DH5α were transformed with 2-5 µL of the reaction and screened via blue/white selection on LB-agar+carbenicillin$^{100}$+X-gal+IPTG. Sequencing screens of 144 colonies per trimer library, typically yielded 90% of all 64 possible clones. All remaining clones in each library were synthesized following the same protocol individually. The FusX system includes five trimer libraries: pFusX1 (64 clones), pFusX2 (64 clones), pFusX3 (64 clones), pFusX4 (64 clones) and pFus_B3 (64 clones). The system also includes one dimer library: pFus_B2 (16 clones). All libraries are available through Addgene. In addition, the collection of 256 pFus_B4 clones are available from Addgene (Ekker Lab TALEN Accessory Pack, cat #1000000038).

Testing and Using the FusX System

TALEN Design

TALEN pairs FLT3 P1, P2 and P3 targeting zebrafish flt3 were described elsewhere (Ma et al., *PLoS ONE,* 8:e65259 (2013)). All other TALENs assembled via the FusX method were designed using Mojo Hand software (Neff et al., *BMC Bioinformatics,* 14:1 (2013), applying the default parameters: an upstream T nucleotide to the TALE domain (Consensus Sequence: Ts.*e); minimum binding length of 15 bp; maximum binding length of 17 (14.5-16.5 RVDs). Spacer minima and maxima were set for 14-17 bp. For every target locus, 1-3 TALEN pairs were saved with a unique restriction site in the middle of the spacer region for a restriction fragment length polymorphism (RFLP) activity assay. Each locus was screened via PCR from pooled genomic DNA (minimum 10 individuals) to confirm efficient amplification and restriction endonuclease digestion while continuing the target sequence prior to committing to a TALEN pair. Newly designed TALENs were assembled into the RCIscript-GoldyTALEN mRNA transcription vector following parameters described below. Assemblies also were performed using a mammalian expression Golden Gate compatible backbone, pC-GoldyTALEN, to ascertain the versatility of this assembly method. These GoldyTALEN receiver vectors are available through Addgene (RCIscript-GoldyTALEN: cat #38142; pC-GoldyTALEN: cat #38143).

3-Day TALEN Assembly Using FusX System

Components for FusX TALEN assembly are set forth in Table 2. Day 1: 7-plasmid assembly were performed similar to the second Golden Gate (GG-2) reaction. For each TALEN repeat array, 50 ng of each component plasmid pFusX1-4, pFus_B2, B3 or B4 and the appropriate pLR were combined with the RCIscript-GoldyTALEN in a 10 μL reaction volume. Reactions were digested with 5 U BsmBI, in 1× NEBuffer 3.1 (New England BioLabs, Ipswich, Mass., USA) for 30 minutes at 55° C., then cooled to 4° C. To each reaction were added 1.5 μL 10× T4 DNA ligase reaction buffer, 400 U T4 DNA Ligase (New England Biolabs, Ipswich, Mass., USA), 5 U Esp3I (Thermo Fisher Scientific, Waltham, Mass., USA), and water to a volume of 15 μL. Reactions were incubated in a thermocycler: (37° C. 5 minutes, 16° C. 10 minutes)×5-6 cycles, 37° C. 15 minutes, 80° C. 5 minutes, and 4° C. hold. To each reaction 0.5 μL ATP (25 mM) and 5 U plasmid-safe DNase (Epicentre, Madison, Wis., USA) were added and incubated at 37° C. for 1 hour, followed by inactivation at 70° C. for 30 minutes. Chemically competent DH5α (min. efficiency $10^7$) were transformed with 2-5 μL of the reaction and screened via blue/white selection on LB-agar+carbenicillin$^{100}$+X-gal+IPTG. Day 2: 4-8 white colonies were screened by colony PCR using primers TAL_F1 (5' TTGGCGTCGGCAAACA-GTGG 3' [SEQ ID NO: 82]) and TAL_R2 (5' GGCGAC-GAGGTGGTCGTTGG 3' [SEQ ID NO: 83]) (Cermak, et al., *Nucleic Acids Res.,* 39:e82 (2011)). For Golden Gate receiver vectors other than RCIscript-GoldyTALEN, colony PCR conditions can be further optimized to predict positive clones. For each TALEN repeat array, 1-2 PCR-positive colonies were selected and cultured in LB+carbenicillin$^{100}$ overnight. Day 3: plasmids were purified from overnight cultures and double-digested with AatII and StuI (New England Biolabs, Ipswich, Mass., USA) to confirm the presence and size of RVD arrays. Each array was sequenced from the forward and reverse direction using primers TAL_F1 and TAL_R2 or using SEQ-TAL-F2 (5' ACCG-CAATGGAGGCAGTG 3' [SEQ ID NO: 84]) and SEQ-TAL-R3 (5' CGTGCGGCAATCCCTTT 3' [SEQ ID NO: 85]). If middle RVDs could not be confirmed, sequencing primer RVD-MM-F (5' CTCACACCCGATCAGGTC 3' [SEQ ID NO: 86]) was used to prime off the $8^{th}$ RVD in the array.

Testing TALENs Somatic Activities In Vivo

RCIscriptGoldyTALEN constructs were linearized by SacI digestion: 5 μg DNA, 10 U SacI (New England Biolabs, Ipswich, Mass., USA), for 6-8 hours at 37° C.). Digested DNA was precipitated by sodium acetate/ethanol extraction, cleaned with 70% ethanol and resuspended in water. Messenger RNA encoding each TALEN arm was in vitro transcribed using the mMESSAGE mMachine T3 Kit (Life Technologies, Grand Island, N.Y., USA), stopped using the supplied ammonium acetate solution and cleaned via phenol:chloroform extraction and isopropanol precipitation (see mMESSAGE mMachine T3 Kit for protocol). TALEN mRNA pairs were injected into one-cell zebrafish embryos at doses ranging from 20-100 pg. Somatic activity for each TALEN pair was analyzed. 72 hour-post-fertilization (hpf) larvae were collected and screened for somatic non-homologous end joining (NHEJ) activity by RFLP assay, described elsewhere (Bedell et al., *Nature,* 491:114-118 (2012); and Ma et al., *PLoS ONE,* 8:e65259 (2013)). In order to quantify the NHEJ activity, ImageJ was used to measure the band intensity. To calculate the percent somatic NHEJ, the undigested band was divided by the sum of both the undigested and digested bands and multiplied by 100.

Sequence Analysis of Somatic Mutations in TALEN (CHD P1) Injected Embryo

Genomic DNA were extracted from representative CHD P1 injected embryos showing ventralizing phenotype, and the targeted chordin locus was PCR amplified with specific primer, pair (Forward: ATTACGCCCCCTTTACGAGC [SEO ID NO: 87]; Reverse: AGCTAGCTACAAACT-CAAGAGCA [SEQ ID NO: 88]). PCR products were TA-cloned with pGEM-T Easy Vector Systems (Promega Corporation, Madison, Wis., US). White colonies were randomly picked and Sanger sequenced with T7 primer (TAATACGACTCACTATAGGG [SEQ ID NO: 89]).

Examining Germline Efficiencies of TALENs

To screen for germline transmission of TALEN-induced mutations, injected fish were out-crossed to obtain F1 embryos. At least eight of the F1 offspring were screened by PCR and subsequent RFLP analyses. First, DNA was isolated from the embryos using an NaOH extraction method (Meeker et al., *BioTechniques,* 43:610-614 (2007)). Next, gene-specific PCR was conducted on individual embryo DNA, and the resulting PCR product was digested to assess germline transmission of the TALEN-induced mutation. To obtain sequence information about TALEN-induced mutations, uncut DNA from the digest was excised from the gel and purified using the QIAGEN QIAEX II Gel extraction kit (Catalog #20021). The purified, uncut DNA was then sequenced using Sanger sequencing and analyzed to determine mutations in the gene corresponding to the TALEN spacer region. Any mutation located in this region was recorded, and the surviving embryos from the clutch were raised.

Results

Modifying Golden Gate TALEN Kit 2.0 into the FusX System

The original GGT Kit requires two rounds of Golden Gate reactions, GG-1 and GG-2, to assemble a full length TAL repeat domain. On Day 1, the user assembles 2-3 partial RVD arrays from monomeric repeat modules. The pFus_A partial arrays present difficulties for some users due to the 11-plasmid digestion/ligation step that can pose an assembly challenge. On Day 3, these partial arrays are assembled in a second digestion/ligation reaction into the full-length binding domain within a functional TAL receiver vector.

The FusX system uses a similar principle as the GGT Kit, but modifies pre-existing components, with the goals of increasing the success rate, shortening the overall process, and reducing the workload of the end user, while maintaining a Golden Gate compatible platform. This was accomplished by:

1) Reducing the number of component plasmids required to obtain a full-length RVD array in a single assembly reaction.
2) Establishing a single assembly reaction, thereby reducing the time required to assemble a full-length RVD array.
3) Minimizing the number of library component (or intermediate) plasmids that make up the FusX system.

The principle of the FusX system was to break down the large partial pFus_A arrays into smaller components. By pre-making smaller modular arrays via the GG-1 reaction, the first 12 repeats of the TAL binding domain are derived from the pFusX1-4 libraries in a scheme of: 3+3+3+3. The remaining repeats of the domain are provided by the pFus_B # libraries (or custom pFus_B # plasmids), and the last, half repeat comes from the pLR. The pFusX1-4 library vectors contained BsmBI overhangs that were sequentially compatible with one another and backward compatible with the original GGT Kit components: pFus_B plasmids, pLR and TAL effector backbones. Table 2 shows the overhangs generated by each BsmBI cleavage event to constrain assembly in a predicted manner into the receiver vector.

Figure 2:
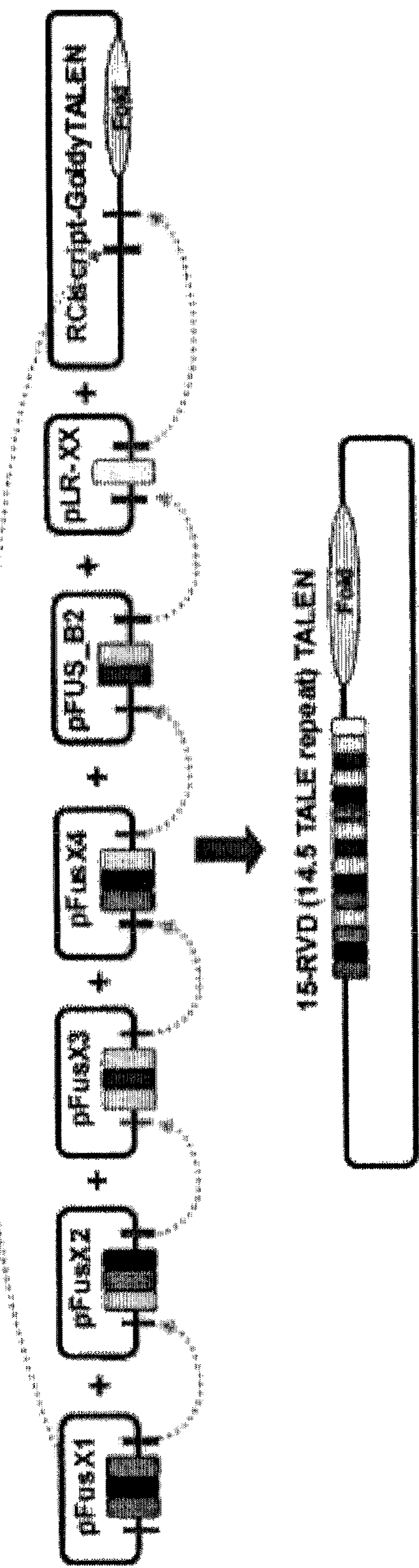
FIG. 2. Using the FusX system to assembly custom TALEN in a single reaction. Dotted arrows indicate the assembly at compatible overhangs generated by BsmBI.

Thus, to assemble a full length DNA binding domain into the final TAL effector backbone, the user assembles one reaction containing: pFusX1 (3 repeats)+pFusX2 (3 repeats)+pFusX3 (3 repeats)+pFusX4 (3 repeats)+pFus_B2-4 (2-4 repeats)+pLR (half repeat) as shown in FIG. 2.

To generate the components of the FusX system, GG-1 was performed to synthesize 7 pre-made libraries of RVD arrays. Each pFusX # library component contained 3 TALE repeat monomers (of which there were 4 carrying different RVDs) for a total of $4^3$=64 plasmids per pFusX # library. The pFus_B # libraries contained 2, 3, or 4 RVD array combinations, for a total of 16, 64, and 256 plasmids per library, respectively (Table 3). Together, these libraries, combined with the last half repeat (pLR) were capable of generating any combination of 14.5, 15.5, or 16.5 module arrays. By building larger custom pFusX_B # plasmids (containing 5-10 RVD array), the user increased the final length of the TAL effector to 17.5-22.5 repeat modules.

Using the FusX System: TALEN Assembling Test

Figure 3:
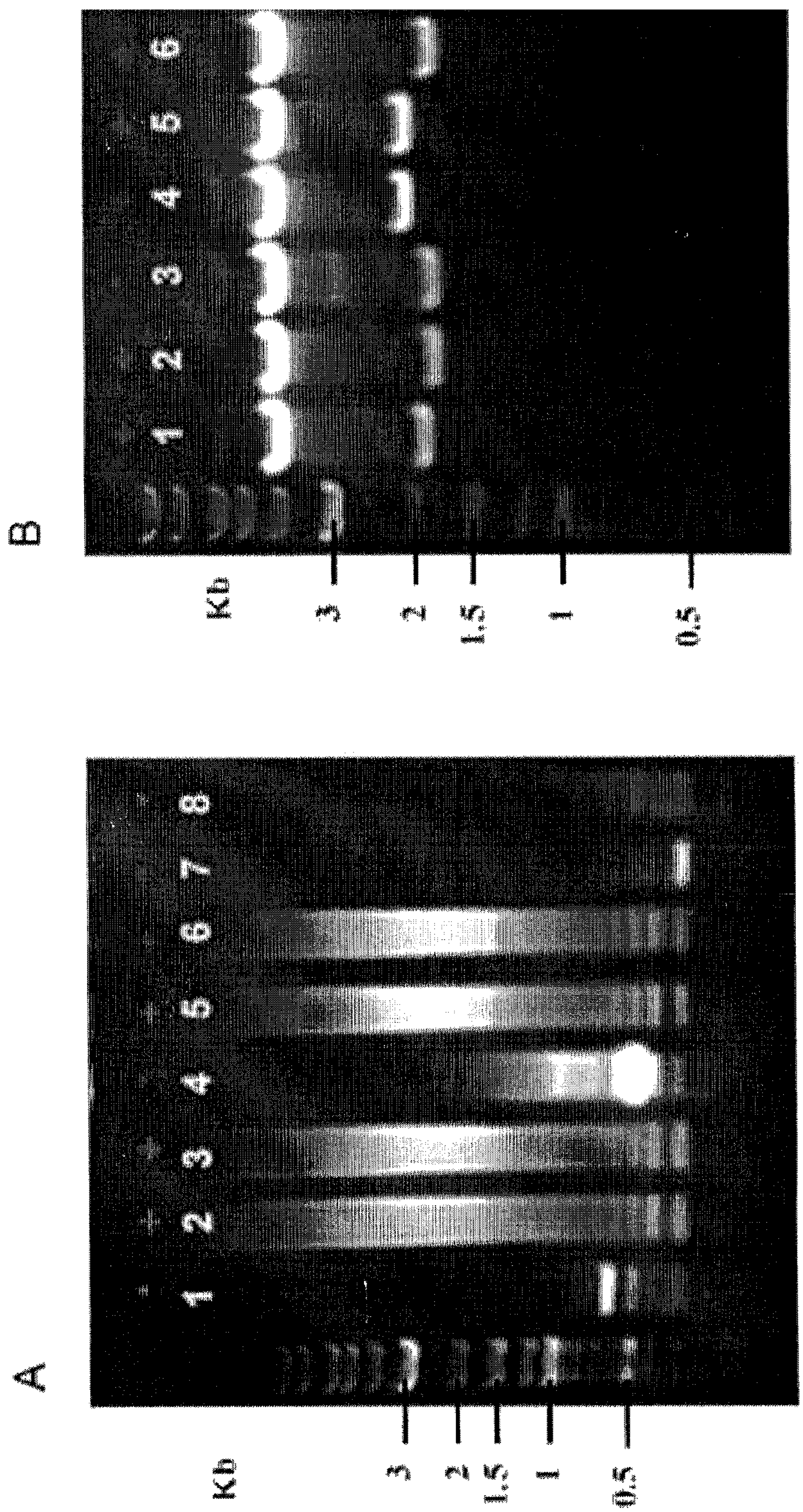
FIG. 3. Screening of correct TALEN assembly by colony PCR and restriction digestion. Representative gel electrophoresis results of colony PCR with primers TAL_F1/TAL_R2 and restriction digestion with AatII/StuI are shown. +: correct TALEN clones; *: incorrect TALEN clones.

More than 160 arrays of 14.5-16.5 RVDs were assembled via the FusX method. A failure to obtain a clone with the correct sequence was not experienced. In 90-95% of cases, screening 1-4 colonies was sufficient to find a positive clone. In about 5-10% of cases, a less favorable assembly was encountered, and up to 8 colonies were screened to identify a correct clone. Generally, if there was a high proportion of white to blue colonies, then a majority, (if not all) of the clones tested (white) were correct. FIG. 3A shows examples of positive and negative colony PCR results, and FIG. 3B shows the size of RVD arrays upon restriction digest by AatII+StuI. Occasionally, a colony that appeared positive by colony PCR, upon digest, contained what appeared to be a mixed population of plasmids (FIG. 3B, lane 3). These mixed populations were not used, but one could simply pick another positive colony from this transformation.

Figure 4:
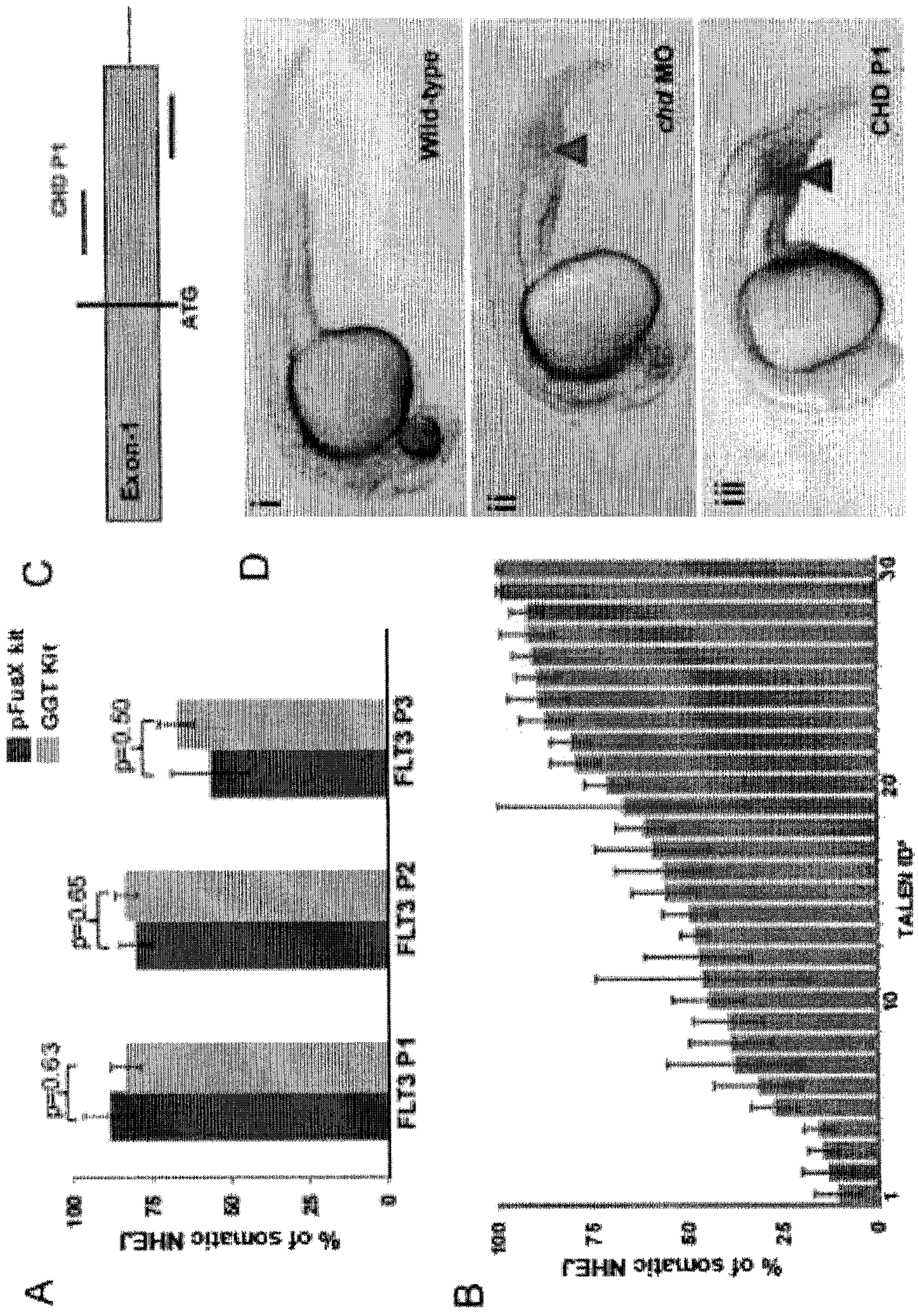
FIG. 4. In vivo mutagenic activity of TALEN pairs assembled with the FusX system. (A) Comparison of somatic efficiency between TALEN pairs (with identical RVD arrays) assembled via FusX system (FLT3 P1X, P2X and P3X) or via the original GGT method (FLT3 P1, P2 and P3 (Ma et al., *PLoS ONE,* 8:e65259 (2013))). Average results of 3 separate experiments analyzing groups of 10 embryos were shown. Error bars represent SEM and efficiencies of TALEN pairs were statistically analyzed with unpaired t-tests. B) Somatic efficiencies of 30 TALEN pairs assembled with the FusX system. Error bars represent SEM. Information of these TALEN pairs are listed in Table 4. C). Design of CHD P1 (TALEN 13) targeting zebrafish chordin Exon-1. D) Embryos injected with CHD P1 (iii) showed significant ICM expansion (arrowhead) at 24 hpf comparing with wild-type (i), phenocopying morpholino-mediated chordin knock-down (iii) (Schulte-Merker et al., *Nature,* 387:862-863 (1997)).

TALEN Pairs Assembled with FusX System have (1) Comparable Activity to Those from GGT Kit, with (2) High Somatic and (3) Germline Activities Using FusX system, three pairs of previously published GoldyTALENs targeting zebrafish flt3: FLT3 P1, P2 and P3, were remade (Ma et al., *PLoS ONE,* 8:e65259 (2013)). All three TALEN pairs (named FLT3 PIX, P2X, and P3X to distinguish from the original pair) were successfully assembled and sequence verified. To test if silent mutations introduced in pFusX3 altered TALEN activity, these newly synthesized TALEN pairs were tested in zebrafish embryos, and their somatic activities were comparable to the previously published original TALEN pairs (FIG. 4A). The somatic efficiency of a larger number of FusX-assembled TALENs were then tested in zebrafish. A collection of 30 TALEN pairs at different loci was designed and assembled (including FLT3 P1-3), and the somatic efficiency of each pair was assessed by RFLP analysis (FIG. 4B and Table 4). Importantly, the range of somatic efficiency (approximately 11-99%) was similar to what was observed using the GoldyTALEN backbone and the original Golden Gate assembly method (Ma et al., *PLoS ONE,* 8:e65259 (2013)). 27 TALEN pairs made using the FusX system were subsequently tested for germline transmission, and all 27 exhibited good transmission of locus-specific alterations (Table 4).

TABLE 4

Somatic activities and germline efficiencies of 30 TALEN pairs synthesized with the FusX system. In vivo somatic activities (% of NEHJ-mediated mutations at somatic level based on RFLP assay) and germline transmission efficiencies of 30 TALEN pairs synthesized with FusX system. FLT P1X, P2X and P3X are independent TALEN pairs targeting different region of flt3 and somatic activities are presented with SEM.

| TALEN | Target | RVD array of TALE domain (5' to 3') | | RFLP-based Somatic | Germline |
|---|---|---|---|---|---|
| ID | gene | Left arm | Rightarm | Efficiency** | Efficiency*** |
| 1 | bsc11 | NN NN NI NN NG NN NN HD NN NN NI NN NI NN NN | NN HD HD NG NI NG NN NI HI HD NG HD HD NG N | 10.6 ± 6.3% | 3/7 |
| 2 | aars2 | NI NG NI NI NI NG NG NI NG NI NI NG NN HD NI NN | NI NI NI NI NN NI HD NN HD HD NI NN NN HD HD NI | 13.1 ± 6.8% | 2/3 |
| 3 | coq7 | NG NN NG NG NN HD HD NN HD NG NN NG NN NN NI | NI NI NN NI NI HD NN NG NI HD HD NG NI NI NG | 14.5 ± 4.0% | 1/6 |
| 4 | micu3a | NI HD NG HD HD NI HD HD NI NN NG NN NG NN NN NI | HD NN NI NI NN NN NG NG HD HD NG NN NI NI HD | 15.6 ± 3.9% | 1/7 |

TABLE 4-continued

Somatic activities and germline efficiencies of 30 TALEN pairs synthesized with the FusX system. In vivo somatic activities (% of NEHJ-mediated mutations at somatic level based on RFLP assay) and germline transmission efficiencies of 30 TALEN pairs synthesized with FusX system. FLT P1X, P2X and P3X are independent TALEN pairs targeting different region of flt3 and somatic activities are presented with SEM.

| TALEN ID | Target gene | RVD array of TALE domain (5' to 3') Left arm | Rightarm | RFLP-based Somatic Efficiency** | Germline Efficiency*** |
|---|---|---|---|---|---|
| 5 | tk2 | HD NI HD HD NI HD NI NN NI HD HD NG NN HD HD | HD HD NG HD NG HD NG NN HD NI HD HD NG HD NG | 27.2 ± 6.2% | 2/2 |
| 6 | ndufab1b | HD HD NI HD HD HD HD NG HD NI HD NI NG NG NI NN | NI NI NN NN NI HD NI NG NI HD NI NN NI NI HD NG | 31.6 ± 11.6% | |
| 7 | micu1 | HD NG NI NN NI NN NG HD HD NI NN HD NI NN HD | HD NG NG HD NG NN NI NN HD HD HD NN HD HD NG HD | 37.8 ± 17.6% | 2/2 |
| 8 | atp5e | NI HD NI NG HD NI NN NN NG NI HD NG HD NG NN HD | HD NI NN NG NN HD NI NN HD HD HD NN HD NI HD NN | 38.7 ± 10.8% | 1/4 |
| 9 | coq2 | HD HD NG HD NN NN NI NN NN NI HD NI NN HD NG HD | NN NG HD HD NG NI HD NG HD NI NN HD HD NG NG NI | 39.3 ± 9.3% | 4/7 |
| 10 | fxn | NI NI NI HD NI NI NI NI NN NI NN NI HD HD NG | NN HD HD NG NG NG NG HD NG NG HD NG HD HD NI | 44.5 ± 9.5% | 2/6 |
| 11 | smdt1 | NG HD HD NN NN NG NN HD HD NN NN NG HD NN NN NG | NN HD NI NN HD NG NN HD NG NN NI NI NN HD HD HD | 46.2 ± 27.9% | 1/2 |
| 12 | cox412b | HD NI NI NI NN NI NN NI NI NN NN NI NN NI NI | HD NG HD HD NG HD HD NG NG NN HD NG NN NI NN NG | 47.2 ± 14.1% | 2/7 |
| 13 | chd (CHDP1) | HD NN HD NI NG HD NG NN NG NN HD NI HD NN NN | NN NN NI NG NN NN NN HD NI NN HD NN HD NN NN | 48.2 ± 3.6% | N/A† |
| 14 | micu2 | NG NG NN HD HD NG HD HD NI NG NN NI NG NI NG | HD NG HD NG NN NN NN NG NN NG HD NI NG NN NG | 49.5 ± 7.0% | |
| 15 | micu3b | NG NG HD NG NG NG HD NN NG HD NG NG HD HD NI NN | NG NN NI NI NI NN HD NG NI NG NG NG NG NI NI | 55.9 ± 8.6% | 3/8 |
| 16 | flt3 (FLTP3X)* | NG NI NN NG NN NG NN HD NI HD NG NG HD NG NN | NI HD HD NI HD HD NG NN NI NN NI NN NG NG NN | 56.3 ± 12.5% | 2/4 |
| 17 | ndufaf6 | NN NN NI NN NN NI HD NI NN NI NN HD NN NG NI HD | HD NG HD HD NI NG NI NN NN HD NG NG HD HD NI | 59.2 ± 14.9% | 1/2 |
| 18 | ndufa9 | NG NN NG NN NI NG HD HD HD NG NG NI HD HD NN | HD NG NN NI NN NN NG NI HD NI NG NN NI NN NI | 61.1 ± 7.6% | 3/8 |
| 19 | pdss2 | NG NG NN NN NN NI NI HD NI NI NN NI NG NN NN | NG NG NN HD HD NI NI HD NI NN NI NI NI NI NG | 66.7 ± 33.3% | 2/12 |
| 20 | cox4i2 | NG NG NN HD HD NI NI HD NI NN NI NI NI N NG | HD HD NG NG HD NG NN HD NG NG HD NI NN NN HD NG | 70.9 ± 5.8% | 2/2 |

TABLE 4-continued

Somatic activities and germline efficiencies of 30 TALEN pairs synthesized with the FusX system. In vivo somatic activities (% of NEHJ-mediated mutations at somatic level based on RFLP assay) and germline transmission efficiencies of 30 TALEN pairs synthesized with FusX system. FLT P1X, P2X and P3X are independent TALEN pairs targeting different region of flt3 and somatic activities are presented with SEM.

| TALEN | Target | RVD array of TALE domain (5' to 3') | | RFLP-based Somatic | Germline |
|---|---|---|---|---|---|
| ID | gene | Left arm | Rightarm | Efficiency** | Efficiency*** |
| 21 | sdha | HD NG NN NG HD NG<br>NN NI NN NN HD HD NN<br>NN HD | NN NN NN NI NI NI<br>NI NN NG NG NG NN<br>NN NG NN NI | 79.2 ± 6.3% | 1/2 |
| 22 | flt3 (FLTP2X)* | NI HD HD HD NI NN HD<br>NI NI NN NI NN HD NG<br>NG | NG NI NN NG NN NG<br>NN HD NI HD NG NG<br>HD NG NN | 80.3 ± 5.2% | 3/3 |
| 23 | mcu | NG HD HD NG NN HD NI<br>NN NN NI NN NN HD NN<br>HD NG | NN NI HD NI NN NG<br>HD NG NN NN NG<br>NN NI HD HD | 87.0 ± 6.7% | 3/3 |
| 24 | flt3 (FLTP1X)* | NN NG NG NI NG NN NG<br>NI NG NG HD NI HD NN<br>HD | NI HD HD HD NI NN<br>HD NI NI NN NI NN<br>HD NG NG | 88.8 ± 8.1% | 2/2 |
| 25 | tmem70 | NN NG NI NI NN NI NG<br>NN NN NG NI HD NI NI<br>NG NG | NI NN NI NG HD NG<br>HD HD NI NG HD NG<br>NG HD NG NN | 89.1 ± 5.5% | 1/2 |
| 26 | cox10 | NN NN NG NI HD NN NI<br>HD NI NN NN NG NG HD<br>NI NN | NI HD HD NI NN NN<br>HD NG HD NI NN NN<br>HD NG NG | 90.4 ± 5.1% | 1/3 |
| 27 | ndufs4 | NI HD HD NI NN NN HD<br>NG HD NI NN NN HD NG<br>NG | HD NG NG NI NI NG<br>NI NG NN HD NG HD<br>HD NG HD NG | 91.8 ± 6.9% | 2/2 |
| 28 | mftmt | HD HD NN NI NI NN NI<br>NI HD NG NN HD NI HD<br>NG | NI NG HD NG NN HD<br>HD NI NI NI NN NG<br>NI NN HD | 91.8 ± 4.2% | 1/2 |
| 29 | ox6b1 | NI NG NI NN NN NN NI<br>NN HD NN NG HD NI NG<br>NN NN | NI NN NG NG HD NG<br>HD HD NI NN HD NG<br>NG HD NG | 98.8 ± 0.9% | 2/4 |
| 30 | surf1 | NG NI NG NG HD NI NN<br>NG HD NN NG HD NI NN<br>NN | NI NI NI NI NG HD<br>NG NN NI NI NG NG<br>NI HD NI HD | 99.0 ± 0.6% | 1/2 |

*Independent TALEN pairs targeting different region of flt3

**Somatic % of NHEJ efficiency determined by RFLP assay with SEM

***Germline efficiency is shown as the number of F0 that gave mutant offspring over the total number of F0 screened.

†Not applicable since ~85% embryos injected with CHD P1 showed ventralized phenotype and were not able to survive into adulthood.

Microhomology-Based Analysis Predicted Loci with Reduced Complexity after Repair DNA double-strand breaks (DSBs) are repaired by a complex set of DNA repair mechanisms that can be classified as either homology based or end joining processes. In most cellular contexts, non-homologous end joining (NHEJ) appears to predominate and can give rise to local sequence alterations including insertions and deletions (indels). A subset of these indels will result in in-frame alterations that may be tolerated or less mutagenic and are therefore less desirable for generating knockouts. Microhomology-mediated end joining (MMEJ) is a Ku- and ligase IV independent DNA repair mechanism that utilizes short regions of sequence microhomology adjacent to the site of DSBs. Lesions that are repaired by MMEJ yield recurrent deletions that appear to be predictable. When coupled with an effective custom enzyme system like TALENs that have a high rate of bi-allelic somatic conversion, microhomology-based selection of TALEN designs can be used to generate predictable out of frame deletion alleles.

The 30 FusX-assembled TALEN collection was assessed for high cutting activity and for potential reduced complexity outcomes likely to be predictive of out-of-frame alleles using a bioinformatic prediction tool (Bae et al., *Nat. Methods,* 11:705-706 (2014); Tables 5 and 6). Four loci were identified with a high pattern score, and these TALENs resulted in modified chromosomes with many carrying predicted sequence outcomes (Tables 5 and 6). For example, the surf1-targeted TALENs were predicted to yield an 8 bp deletion, and 78% of the assessed chromosomes carried this specific DNA change (Tables 5 and 6).

TABLE 5

Sequences of somatic mutation in CHD P1 injected embryos. Sequences of the targeted chordin locus in two individual embryos injected with TALEN (CHD P1). 14 separated clones from each embryo were shown. Boxed are TALEN (CHD P1) binding site and highlighted are BcoDI recognition site used in RFLP assay.

Wild-type

[SEQ ID NO: 90]
CGTTATTATCGCATCTGTGCACGGATCGAGACTCAAGACACCCGCGCTGCCCATCCAGCCCGAGA

Embryo 1

[SEQ ID NO: 91]
CGTTATTATCGCATCTGTGCACGGATCGAGACTCAAGACACCCGCGCTGCCCATCCAGCCCGAGA

[SEQ ID NO: 92]
CGTTATTATCGCATCTGTGCACGGATCGA-------GACACCCGCGCTGCCCATCCAGCCCGAGA

[SEQ ID NO: 93]
CGTTATTATCGCATCTGTGCACGGATC---------GACACCCGCGCTGCCCATCCAGCCCGAGA

[SEQ ID NO: 94]
CGTTATTATCGCATCTGTGCACGGATCGA-------GACACCCGCGCTGCCCATCCAGCCCGAGA

[SEQ ID NO: 95]
CGTTATTATCGCATCTGTGCACGGATC-------AAGACACCCGCGCTGCCCATCCAGCCCGAGA

[SEQ ID NO: 96]
CGTTATTATCGCATCTGTGCACGGATCGA-------GACACCCGCGCTGCCCATCCAGCCCGAGA

[SEQ ID NO: 97]
CGTTATTATCGCATCTGTGCACGGATCGAG-C-----ACACCCGCGCTGCCCATCCAGCCCGAGA

[SEQ ID NO: 98]
CGTTATTATCGCATCTGTGCACGGATCGAGACT--AGACACCCGCGCTGCCCATCCAGCCCGAGA

[SEQ ID NO: 99]
CGTTATTATCGCATCTGTGCACGG----------AAGACACCCGCGCTGCCCATCCAGCCCGAGA

[SEQ ID NO: 100]
CGTTATTATCGCATCTGTGCACGGA---------AAGACACCCGCGCTGCCCATCCAGCCCGAGA

[SEQ ID NO: 101]
CGTTATTATCGCATCTGTGCACGGATCGA-------GACACCCGCGCTGCCCATCCAGCCCGAGA

[SEQ ID NO: 102]
CGTTATTATCGCATCTGTGCACGGAT---------AGACACCCGCGCTGCCCATCCAGCCCGAGA

[SEQ ID NO: 103]
CGTTATTATCGCATCTGTGCACGGATCGA-------GACACCCGCGCTGCCCATCCAGCCCGAGA

[SEQ ID NO: 104]
CGTTATTATCGCATCTGTGCACGGATCGA-------GACACCCGCGCTGCCCATCCAGCCCGAGA

Embryo 2

[SEQ ID NO: 105]
CGTTATTATCGCATCTGTGCACGG------------ACACCCGCGCTGCCCATCCAGCCCGAGA

[SEQ ID NO: 106]
CGTTATTATCGCATCTGTGCACGGATCGA-------GACACCCGCGCTGCCCATCCAGCCCGAGA

[SEQ ID NO: 107]
CGTTATTATCGCATCTGTGCACGGATCGA-------GACACCCGCGCTGCCCATCCAGCCCGAGA

[SEQ ID NO: 108]
CGTTATTATCGCATCTGTGCACGGATC---------GACACCCGCGCTGCCCACCCAGCCCGAGA

[SEQ ID NO: 109]
CGTTATTATCGCATCTGTGCACGGA----------AGACACCCGCGCTGCCCATCCAGCCCGAGA

[SEQ ID NO: 110]
CGTTATTATCGCATCTGTGCACGGATCGA-------GACACCCGCGCTGCCCATCCAGCCCGAGA

[SEQ ID NO: 111]
CGTTATTATCGCATCTGTGCACGG------------------------CCCATCCAGCCCGAGA

TABLE 5-continued

Sequences of somatic mutation in CHD P1 injected embryos. Sequences of the targeted chordin locus in two individual embryos injected with TALEN (CHD P1). 14 separated clones from each embryo were shown. Boxed are TALEN (CHD P1) binding site and highlighted are BcoDI recognition site used in RFLP assay.

[SEQ ID NO: 112]
CGTTATTATCGCATCTGTGCACGGATCGA-------GACACCCGCGCTGCCCATCCAGCCCGAGA

[SEQ ID NO: 113]
CGTTATTATCGCATCTGTGCACGGATCGA-------GACACCCGCGCTGCCCATCCAGCCCGAGA

[SEQ ID NO: 114]
CGTTATTATCGCATCTGTGCACGGATC---------GACACCCGCGCTGCCCACCCAGCCCGAGA

[SEQ ID NO: 115]
CGTTATTATCGCATCTGTGCACGGAT---------AGACACCCGCGCTGCCCATCCAGCCCGAGA

[SEQ ID NO: 116]
CGTTATTATCGCATCTGTGCACGGATCGA-------GACACCCGCGCTGCCCATCCAGCCCGAGA

[SEQ ID NO: 117]
CGTTATTATCGCATCTGTGCACGGATCGA-------GACACCCGCGCTGCCCATCCAGCCCGAGA

[SEQ ID NO: 118]
CGTTATTATCGCATCTGTGCACGGATCGA-------GACACCCGCGCTGCCCATCCAGCCCGAGA

Two embryos were analyzed, and each sequence represents a separated clone sequenced. Boxed are TALEN (CHD P1) binding site, and highlighted are BcoDI recognition site used in RFLP assay.

TABLE 6

Microhomology to predict TALEN mutations. Using the algorithm described in Bae. et al., the top pattern score and its associated microhomology score were calculated for each locus. The top predicted deletion pattern that would be expected based on local microhomology are also shown. TALEN somatic cutting efficiency at each locus was determined in individual fish and the number of sequenced clones exhibiting the expected deletion pattern was calculated.

| Target Gene | Micro-homology Score | op Pattern Score | Deletion length | SEQ ID NO: | Predicted Pattern | Percent of clones with Predicted Pattern | Somatic Efficiency* |
|---|---|---|---|---|---|---|---|
| surf1 | 2512.7 | 70.0 | 8 bp | 119 | TATTCAGACGTCAGGATGCTCC --------GGTGTAATTCAGATTTT | 77.8 % (n = 9) | 81.8% (n = 11) |
| chd (P1) | 3498.4 | 23.0 | 7 bp | 120 | CGCATCTGTGCACGGATCGAGA C-------ACCCGCGCTGCCCATCC | 55.6% (n = 27) | 96.4% (n = 28) |
| pdss2 | 3296.3 | 46.3 | 10 bp | 121 | TTGGGAACAAGATGGCGGT----- -----GATTTTCTGTTGGCAA | 42.9 % (n = 14) | 100% (n = 14) |
| cox10 | 2760.4 | 24.9 | 10 bp | 122 | GGTACGACAGGTTCAGC---------- ------CTTAAAGCCTGAGCCTGGT | 50% 4 bp ins, 25% 33 bp ins (n = 8)** | 72.7% (n = 11) |
| ndufa9 | 2602.0 | 55.2 | 9 bp | 123 | TGTGATCCCTTACCGAT-GTGA-------- ------TCTCATGTACCTCAG | 20.0 % (n = 5) | 55.5% (n = 9) |
| ndufs4 | 1958.0 | 64.7 | 2 bp | 124 | GTCAGGACATCTCAACTC-------- ----CAGAGGAGCATATTAAG | 8.3 % (n = 12) | 100% (n = 12) |

*Somatic efficiency based on sequencing results from cloned PCR products from individual fish.
**Cox10 showed multiple insertions, which are not predicted by the algorithm.

The use of this for somatic gene targeting is exemplified by the TALEN pair (CHD P1) targeting zebrafish chordin exon-1 (FIG. 4C). Zebrafish chordin is a BMP antagonist, and homozygous chordin mutant (chordino) (Schulte-Merker et al., *Nature,* 387:862-863 (1997)) or morpholino-mediated knockdown embryos (Leung et al., *Dev. Biol.,* 277:235-254 (2005)) exhibit strong cell fate changes due to enhanced BMP signaling; an effect that is readily visualized by a characteristic expansion of the intermediate-cell-mass (ICM). The microhomology prediction algorithm developed by Bae et al. (*Nat. Methods,* 11:705-706 (2014)) indicated these TALENs would likely result in a 7 bp deletion (Table 6); a result confirmed by DNA sequencing of the chromosomes of injected embryos (96.4% modified total, with 56% of the predicted 7 bp outcome). This highly efficient method for somatic mutagenesis also was confirmed by phenotypic analyses; 85.2±7.4% of TALEN injected embryos exhibited the recessive ventralizing phenotype at 24 hpf, phenocopying morpholino-mediated chordin knockdown with high penetrance (FIG. 4C). The RFLP analysis (Table 4) underestimated the activity of this particular TALEN pair because the BcoDI restriction site used for this particular RFLP assay was recapitulated following the predicted 7 bp deletion that resulted from MMEJ repair (Table 6).

One example where the microhomology-based prediction resulted in an indeterminate outcome was noted. The TALENs against cox10 were predicted to yield a 10 bp deletion based on the outcome with the highest microhomology score (Table 6). 75% of the chromosomes carried one of two specific DNA repair outcomes. However, instead of deletions, these were 4 and 33 bp insertions (Table 6). An alternative synthesis dependent (SD) form of microhomology-mediated end joining (SD-MMEJ) that utilizes non-processive DNA polymerases to create regions of microhomology was proposed to explain this outcome (Yu and McVey, *Nucleic Acids Res.,* 38:5706-5717 (2010)).

In some respects, the FusX system is a modified version of the GGT Kit. Instead of 10-repeats TALE intermediates, pre-assembled trimers were used and TALE domain between 14.5 to 16.5 repeats can be assembled in a single Golden Gate reaction. Previously reported as well as newly designed TALEN pairs were assembled using the FusX system and tested in vivo in zebrafish embryos. Correct sequences of all 30 pairs of TALEN synthesized verified the assembly system, and a comparable range of somatic efficiencies, in particular, between FLT3 P1, P2 and P3 and FLT3 P1X, P2X and P3X, respectively, suggested that silent mutations introduced in pFusX3 do not affect TALEN activity. Somatic mutagenic efficiency also was tested phenotypically with CHD P1 targeting BMP antagonist chordin. Since the characteristics ventralization in chordino mutant is recessive, the moderate (>50%) somatic efficiency of CHD P1 is incompatible with its high penetrance. Two representative embryos (showing obvious ICM expansion with ~50% somatic efficiency in RFLP assay) were subsequently analyzed by sequencing and small frame-shifting deletions recapitulating the restriction site for RFLP assay were identified in more than 50% of analyzed clones, explaining the discrepancy between RFLP predicted efficiency and the observed high penetrance. In fact, in select circumstances, this phenomenon may lead to recurrent underestimation of GoldyTALEN efficiency as predicted by RFLP assay only.

Since the one-step Golden Gate reaction with FusX system is almost identical to the second round Golden Gate reaction in GGT Kit. Both kits use common, inexpensive molecular reagents, and no alternative reagents are required when switching from the GGT Kit to FusX system. Importantly, FusX system is backward compatible with the GGT Kit making all TALE effector scaffolds previously constructed for the GGT Kit available for use with pFusX assembly. Moreover, because the FusX system is compatible to all pFus_B # vectors, it retains the flexibility to assemble TALE domains with up to 22.5 repeats. However, pFus_B5 to pFus_B10 are required to assemble TAL domains longer than 16.5 repeats and would need to be made separately using the original GGT Kit. Finally, sequencing primers can be designed to target the silent mutations introduced in pFusX3 at TALE repeat 8, ensure complete sequencing of the final TALE domain.

Besides TALEN-mediated genome editing, the applications of non-nuclease TAL effectors are also promising, which includes transcription activator/repressors (Crocker and Stern, *Nat. Methods,* 10:762-767 (2013); and Cong et al., *Nat. Commun.,* 3:968 (2012), DNA and histone methylation modifiers (Maeder et al., *Nat. Biotechnol.,* 31:1137-1142 (2013); and Mendenhall et al., *Nat. Biotechnol.,* 31:1133-1136 (2013)), and fluorescent DNA visualizer (Thanisch et al., *Nucleic Acids Res.,* 42:e38 (2014)). Similar to TALEN-based methods, all these applications involves the fusion of TALE DNA binding domain with particular functional domains (e.g. VP64, Hairy/SID/KRAB Repression domain, lysine-specific demethylase, TET1 hydroxylase catalytic domain, GFP etc.), which could be substituted for the FokI catalytic domain to generate new compatible destination vectors. And with these new destination vectors, the FusX system can be used immediately for to synthesize a wide-range of non-nuclease TAL effectors.

There are two possible considerations involving the FusX system. The first is the requirement to establish a collection of component plasmids before initiating any synthesis reactions. With all seven libraries to assembled TALE domain from 14.5 to 16.5 repeats, there are 592 plasmids in total excluding the four pLR and TALE effector backbones. However, the core components for assembling TALE domain with 14.5 repeats (pFusX1 to 4 and pFus_B2), which was used in this example, only consists of 272 plasmids. Secondly, the presented FusX system only includes the most standard RVD ciphers; alternative RVDs, such as NH and N* are not included. For a complete switch to an alternative RVD, such as replacing all NN with NH, libraries can be recreated using receiver plasmids available in the pFusX system. However, if alternative RVD(s) is only required in certain repeat(s), one will need to assemble corresponding pFusX or pFus_B # clone(s) separately. This latter alternative assembling process is still advantageous over the older platform as it can be accomplished within five days, and the efficiency of assembling 3-repeat intermediates is much higher than that of a 10-repeats intermediate.

In summary, the FusX TALE assembly system presented herein provides a backward compatible upgrade of the successful GGT Kit with a shorter protocol. Yet, the FusX system retains high flexibility on the length of TALE domains, compatibility with other non-nuclease TAL effector applications, and potential for future incorporation of alternative RVDs. The assembly method described herein uses standard molecular biology equipment and laboratory skills that can be easily adopted for small-scale TALEN production at high efficiency. These libraries also can be formatted into multi-well plates and hence coupled with modern automation equipment for high throughput semi-automatic TALEN synthesis for large-scale genome editing, an approach that has been shown to be effective for rapid TALE assembly (Reyon et al., *Nat. Biotechnol.,* 30:460-465 (2012); and Liang et al., *ACS Synth. Biol,* 3:67-73 (2014)). Thus, the FusX system would benefit from but does not require such expensive capital equipment. FusX is a high-throughput assembly system that maintains the highest level of backward compatibility with prior genome science expression systems.

Example 2

Figures 5A, 5B, 5C, 5D:
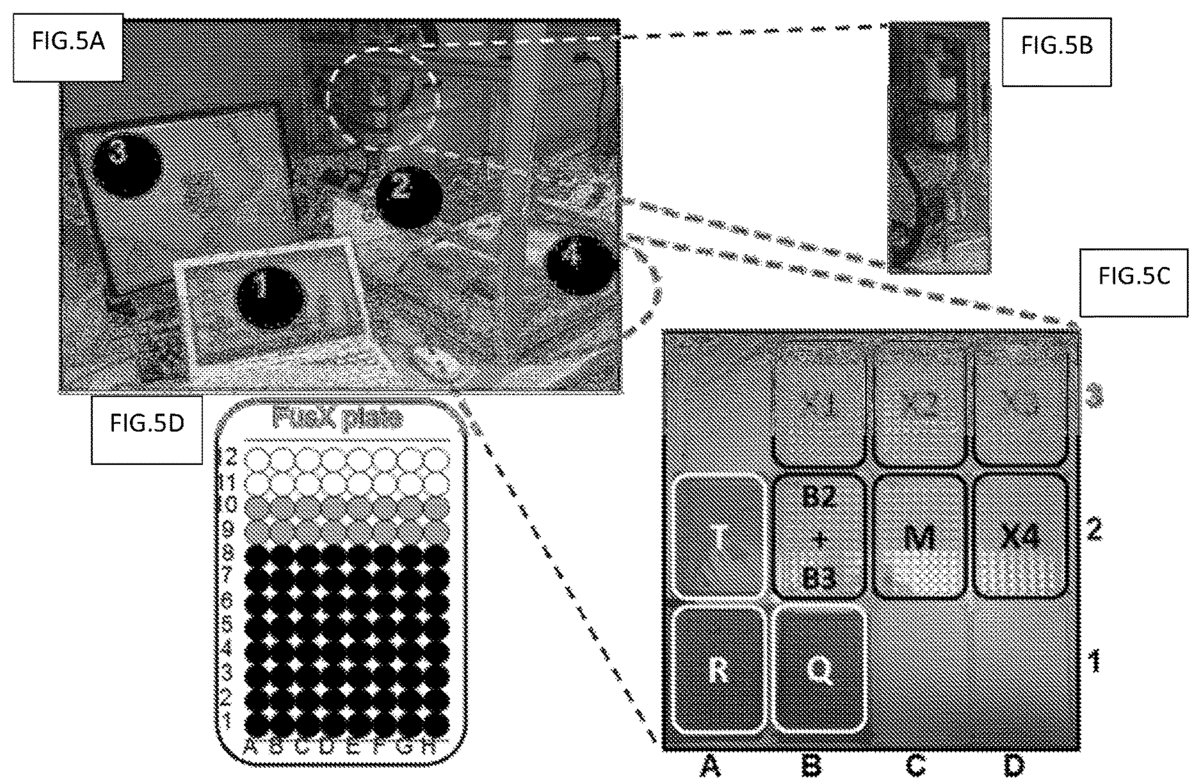
FIG. 5. Enhanced FusX assembly using an automated liquid handling laboratory automation tool. A. OT. One liquid handling robot (LHR) set up for TALEN arm assembly via FusX system. The MacBook laptop (1) operates the graphical user interface of the LHR software running on a Raspberry Pi 2 (RPi) single-board computer (2). The RPi takes the JSON script of an arbitrary protocol and parses it into a G-code job to be run by the Smoothieboard numerical controller (2). A monitor connected to RPi via HDMI to visualize the RPi OS (GNU/Linux 8.0) (3). LHR workspace (4). B. DRAGONLAB 10μ micropipette. C. Zoom-in on LHR workspace. Black border: six 96-well plates containing the RVD libraries pFusX1-X4, pFus_B2+B3, and an extra plate (M) with the receiver backbone plasmid and the pLR plasmid stocks. White border: 10 μl tip rack (R), trash bin (T), and destination aliquots for TALEN arm assembly (Q). D. Organization of the pFusX 96-well plates. In black, all 64 possible combinations of RVD plasmids were arranged based on the output from the Mojo Hand inventory-management software for TALEN arm assembly for libraries pFusX1-pFusX4 and pFus_B3. In gray, the 16 extra wells for plasmid pFus_B2 in the pFusB2+B3 plate.

Programming TALENs Using an Accessible Laboratory Automation Tool, OpenTrons All 64 RVD plasmids of each pFusX1-pFusX4 trimer library were organized by columns (starting with column A) into four 96-well plates (FIG. 5D). An additional 96-well plate was used to store the 64 pFus_B3 RVD and the 16 pFus_B2 RVD plasmids. The RVD plasmids were mapped onto the appropriate plate in alphabetical order of the nucleotide sequence of their target recognition site (i.e. AAA, AAC, AAG, AAT, ACA, ACC, and so on). A sixth 96-well plate was used to store aliquots of the 4 pLR plasmids in the same alphabetical order as above, the GoldyTALEN receiver plasmid, and the 10x Buffer 3.1 (NEB) from well A1 (NI pLR plasmid) to F1(10x Buffer 3.1) accordingly. An OT.One Opentrons LHR (firmware v1.0.0pipy, FIG. 5A), running on a Raspberry Pi 2 singleboard computer (Raspbian GNU/Linux 8.0 (jessie)) and a Smoothieboard 5x numerical controller (SmoothiewareOT v1.0.5, FIG. 5A and object labeled 2), was set up to handle a 10μ.DRAGONLAB micropipette (FIG. 5B) and was connected via Ethernet to a MacBook laptop (2.2 GHz Intel Core Duo processor and 4 GB 667 MHz DDR2 SDRAM memory, operating on Mac OS X version 10.7.5, FIG. 5A and object labeled 1) following the instructions provided by the manufacturer. Next, the six flat-bottom 96-well plates described above, a trash bin, a tip rack, and destination rack for the TALEN arm assemblies were placed in designated sockets of the LHR (FIG. 5C). The set-up used is shown in FIG. 5A (objects labeled 1-4).

The LHR was calibrated as recommended by the manufacturer. Briefly, the 3D coordinates of the position of the A1 well were mapped into the LHR software for all plates. Subsequently, the z-coordinates of the functional positions of the pipette plunger were assigned (starting point, liquid blowout point, and tip ejection point). The JSON (JavaScript Object Notation) file encoding the liquid handling protocol for TALEN arm assembly was generated using the online editor tool provided by the manufacturer. The protocol used in this study consisted on the successive transfer of the appropriate RVD plasmid from all FusX system libraries and the receiver plasmid into a destination tube per TALEN arm for seven different TALEN arm sequences. The JSON file used for this specific experiment will be provided upon email request to the corresponding author.

Day one of the manual. FusX protocol was modified to account for the micropipette used by the LHR. Both the RVD plasmid stocks and the receiver plasmid GoldyTALEN were diluted 5-fold so that 5 μL were pipetted into the TALEN arm aliquot instead of the standard 1 μL. In parallel, two other aliquots were pipetted manually per TALEN arm as positive controls: one using the LHR-modified protocol and another using the standard protocol. Next, 1μ of the restriction enzyme BsmB1 (NEB cat # R0580) and 1.2 μL of 10× Buffer 3.1 (NEB) were added to 10 μL of each manual repeat. For each TALEN arm, all three aliquots were treated following the standard FusX protocol.

Result: TALEN programming using an accessible laboratory automation tool. The FusX system is designed support robotic liquid handling to minimize human-derived technical errors and for enhanced scalability (FIG. 5). All 64 RVD combinations of plasmids pFusX1-pFusX4 and pFus_B3, and the 16 RVD combinations of plasmid pFus_B2 were mapped onto 96-well plates as shown in FIG. 5D. The mapping configuration can be synced with an inventory management and/or TALEN design software of preference (e.g. Mojo Hand). In turn, the position of each 96-well plate was mapped in a grid onto the workspace of an OT. One liquid handling robot (LHR, FIG. 5C). Thus, any desired RVD sequence can be systematically consolidated into a single aliquot using an LHR device if the coordinates of every well in every plate are known. Liquid handling robotics was used to aliquot the RVD sequence for 16 TALEN arms. Positive controls were made by manually assembling the RVDs of ten of the TALEN arms in parallel to the robot assemblies. Sequencing data confirmed the successful assembly of all TALEN arms, whether pipetted manually or robotically.

We claim:

1. A method for assembling a polynucleotide sequence that encodes a transcription activator-like effector (TALE)-DNA modifying enzyme that comprises (A) a TALE binding domain comprising a plurality of repeat modules, and (B) a DNA modifying enzyme domain, wherein the method comprises combining, in a single reaction mixture, (a) a plurality of DNA segments, wherein an individual DNA segment of said plurality of DNA segments encodes a repeat module of said TALE binding domain repeat modules, and wherein said plurality of DNA segments comprises at least two trimer DNA sequences, and b) a first expression vector encoding said DNA modifying enzyme domain wherein said combining is under conditions so as to generate a second expression vector encoding said polynucleotide sequence encoding said TALE-DNA modifying enzyme in a single cloning reaction.

2. The method of claim 1, wherein said TALE binding domain comprises n repeat modules, wherein n is an integer, and said reaction mixture comprises from two of said trimer DNA sequences to n/3 trimer DNA sequences.

3. The method of claim 2, wherein said reaction mixture comprises n/3 trimer DNA sequences.

4. The method of claim 2, wherein said reaction mixture comprises (n−1)/3 trimer DNA sequences.

5. The method of claim 2, wherein said reaction mixture comprises (n−2)/3 trimer DNA sequences.

6. The method of claim 2, wherein said reaction mixture comprises (n−3)/4 trimer DNA sequences.

7. The method of claim 1, wherein said TALE binding domain further comprises a portion of a repeat module that is operably linked at the C-terminal end of said plurality of repeat modules, and wherein said method further comprises combining, in said single reaction mixture, a DNA sequence encoding said portion of a repeat module.

8. The method of claim 7, wherein said DNA sequence encoding said portion of a repeat module is comprised in an expression vector.

9. The method of claim 1, wherein each trimer DNA sequence of said at least two trimer DNA sequences is comprised in an expression vector.

10. The method of claim 1, wherein said single reaction mixture further comprises one or more restriction enzymes and one or more DNA ligases.

11. The method of claim 1, wherein said method further comprises purifying the generated polynucleotide sequence encoding said TALE-DNA modifying enzyme.

12. The method of claim 1, wherein said method is automated.

13. The method of claim 1, wherein said second expression vector is produced within five days of said combining.

14. The method of claim 13, wherein said second expression vector is produced within three days of said combining.

15. The method of claim 1, wherein said combining produces at least 90% assembled said polynucleotide sequence.

* * * * *

SEQUENCE LISTING

```
<160> NUMBER OF SEQ ID NOS: 124

<210> SEQ ID NO 1
<211> LENGTH: 82
<212> TYPE: DNA
<213> ORGANISM: Artificial sequence
<220> FEATURE:
<223> OTHER INFORMATION: Synthetic

<400> SEQUENCE: 1

ccggtggtct ctggcggcaa gcaagcgctc gaaacggtgc agcggctgtt gccggtgctg     60

tgccaggacc atggcgagac gt                                             82


<210> SEQ ID NO 2
<211> LENGTH: 74
<212> TYPE: DNA
<213> ORGANISM: Artificial sequence
<220> FEATURE:
<223> OTHER INFORMATION: Synthetic

<400> SEQUENCE: 2

ctcgccatgg tcctggcaca gcaccggcaa cagccgctgc accgtttcga gcgcttgctt     60

gccgccagag acca                                                      74


<210> SEQ ID NO 3
<211> LENGTH: 30
<212> TYPE: DNA
<213> ORGANISM: Artificial sequence
<220> FEATURE:
<223> OTHER INFORMATION: Synthetic
```

<400> SEQUENCE: 3
attcttaagc gtctccatgg cctgaccccg 30

<210> SEQ ID NO 4
<211> LENGTH: 28
<212> TYPE: DNA
<213> ORGANISM: Artificial sequence
<220> FEATURE:
<223> OTHER INFORMATION: Synthetic

<400> SEQUENCE: 4
attgacgtct cgcaggccat ggtcctgg 28

<210> SEQ ID NO 5
<211> LENGTH: 26
<212> TYPE: DNA
<213> ORGANISM: Artificial sequence
<220> FEATURE:
<223> OTHER INFORMATION: Synthetic

<400> SEQUENCE: 5
gttcttaagc gtctcccctg accccg 26

<210> SEQ ID NO 6
<211> LENGTH: 25
<212> TYPE: DNA
<213> ORGANISM: Artificial sequence
<220> FEATURE:
<223> OTHER INFORMATION: Synthetic

<400> SEQUENCE: 6
gttgacgtct cggccatggt cctgg 25

<210> SEQ ID NO 7
<211> LENGTH: 11
<212> TYPE: DNA
<213> ORGANISM: Artificial sequence
<220> FEATURE:
<223> OTHER INFORMATION: Synthetic

<400> SEQUENCE: 7
cgtctccccc t 11

<210> SEQ ID NO 8
<211> LENGTH: 11
<212> TYPE: DNA
<213> ORGANISM: Artificial sequence
<220> FEATURE:
<223> OTHER INFORMATION: Synthetic

<400> SEQUENCE: 8
agggggagac g 11

<210> SEQ ID NO 9
<211> LENGTH: 11
<212> TYPE: DNA
<213> ORGANISM: Artificial sequence
<220> FEATURE:
<223> OTHER INFORMATION: Synthetic

<400> SEQUENCE: 9
ctgacgagac g 11

<210> SEQ ID NO 10

<211> LENGTH: 11
<212> TYPE: DNA
<213> ORGANISM: Artificial sequence
<220> FEATURE:
<223> OTHER INFORMATION: Synthetic

<400> SEQUENCE: 10
cgtctcgtca g 11

<210> SEQ ID NO 11
<211> LENGTH: 11
<212> TYPE: DNA
<213> ORGANISM: Artificial sequence
<220> FEATURE:
<223> OTHER INFORMATION: Synthetic

<400> SEQUENCE: 11
cgtctccctg a 11

<210> SEQ ID NO 12
<211> LENGTH: 11
<212> TYPE: DNA
<213> ORGANISM: Artificial sequence
<220> FEATURE:
<223> OTHER INFORMATION: Synthetic

<400> SEQUENCE: 12
tcagggagac g 11

<210> SEQ ID NO 13
<211> LENGTH: 11
<212> TYPE: DNA
<213> ORGANISM: Artificial sequence
<220> FEATURE:
<223> OTHER INFORMATION: Synthetic

<400> SEQUENCE: 13
atggcgagac g 11

<210> SEQ ID NO 14
<211> LENGTH: 11
<212> TYPE: DNA
<213> ORGANISM: Artificial sequence
<220> FEATURE:
<223> OTHER INFORMATION: Synthetic

<400> SEQUENCE: 14
cgtctcgcca t 11

<210> SEQ ID NO 15
<211> LENGTH: 11
<212> TYPE: DNA
<213> ORGANISM: Artificial sequence
<220> FEATURE:
<223> OTHER INFORMATION: Synthetic

<400> SEQUENCE: 15
cgtctccatg g 11

<210> SEQ ID NO 16
<211> LENGTH: 11
<212> TYPE: DNA
<213> ORGANISM: Artificial sequence
<220> FEATURE:
<223> OTHER INFORMATION: Synthetic

<400> SEQUENCE: 16
ccatggagac g 11

<210> SEQ ID NO 17
<211> LENGTH: 11
<212> TYPE: DNA
<213> ORGANISM: Artificial sequence
<220> FEATURE:
<223> OTHER INFORMATION: Synthetic

<400> SEQUENCE: 17
cctgcgagac g 11

<210> SEQ ID NO 18
<211> LENGTH: 11
<212> TYPE: DNA
<213> ORGANISM: Artificial sequence
<220> FEATURE:
<223> OTHER INFORMATION: Synthetic

<400> SEQUENCE: 18
cgtctcgcag g 11

<210> SEQ ID NO 19
<211> LENGTH: 11
<212> TYPE: DNA
<213> ORGANISM: Artificial sequence
<220> FEATURE:
<223> OTHER INFORMATION: Synthetic

<400> SEQUENCE: 19
cgtctcccct g 11

<210> SEQ ID NO 20
<211> LENGTH: 11
<212> TYPE: DNA
<213> ORGANISM: Artificial sequence
<220> FEATURE:
<223> OTHER INFORMATION: Synthetic

<400> SEQUENCE: 20
caggggagac g 11

<210> SEQ ID NO 21
<211> LENGTH: 11
<212> TYPE: DNA
<213> ORGANISM: Artificial sequence
<220> FEATURE:
<223> OTHER INFORMATION: Synthetic

<400> SEQUENCE: 21
tggccgagac g 11

<210> SEQ ID NO 22
<211> LENGTH: 11
<212> TYPE: DNA
<213> ORGANISM: Artificial sequence
<220> FEATURE:
<223> OTHER INFORMATION: Synthetic

<400> SEQUENCE: 22
cgtctcggcc a 11

<210> SEQ ID NO 23
<211> LENGTH: 11
<212> TYPE: DNA

<213> ORGANISM: Artificial sequence
<220> FEATURE:
<223> OTHER INFORMATION: Synthetic

<400> SEQUENCE: 23
cgtctcatgg c 11

<210> SEQ ID NO 24
<211> LENGTH: 11
<212> TYPE: DNA
<213> ORGANISM: Artificial sequence
<220> FEATURE:
<223> OTHER INFORMATION: Synthetic

<400> SEQUENCE: 24
gccatgagac g 11

<210> SEQ ID NO 25
<211> LENGTH: 11
<212> TYPE: DNA
<213> ORGANISM: Artificial sequence
<220> FEATURE:
<223> OTHER INFORMATION: Synthetic

<400> SEQUENCE: 25
ctatcgagac g 11

<210> SEQ ID NO 26
<211> LENGTH: 11
<212> TYPE: DNA
<213> ORGANISM: Artificial sequence
<220> FEATURE:
<223> OTHER INFORMATION: Synthetic

<400> SEQUENCE: 26
cgtctcgata g 11

<210> SEQ ID NO 27
<211> LENGTH: 11
<212> TYPE: DNA
<213> ORGANISM: Artificial sequence
<220> FEATURE:
<223> OTHER INFORMATION: Synthetic

<400> SEQUENCE: 27
cgtctcatgg c 11

<210> SEQ ID NO 28
<211> LENGTH: 11
<212> TYPE: DNA
<213> ORGANISM: Artificial sequence
<220> FEATURE:
<223> OTHER INFORMATION: Synthetic

<400> SEQUENCE: 28
gccatgagac g 11

<210> SEQ ID NO 29
<211> LENGTH: 11
<212> TYPE: DNA
<213> ORGANISM: Artificial sequence
<220> FEATURE:
<223> OTHER INFORMATION: Synthetic

<400> SEQUENCE: 29
ctatcgagac g 11

<210> SEQ ID NO 30
<211> LENGTH: 11
<212> TYPE: DNA
<213> ORGANISM: Artificial sequence
<220> FEATURE:
<223> OTHER INFORMATION: Synthetic

<400> SEQUENCE: 30
cgtctcgata g 11

<210> SEQ ID NO 31
<211> LENGTH: 11
<212> TYPE: DNA
<213> ORGANISM: Artificial sequence
<220> FEATURE:
<223> OTHER INFORMATION: Synthetic

<400> SEQUENCE: 31
cgtctcatgg c 11

<210> SEQ ID NO 32
<211> LENGTH: 11
<212> TYPE: DNA
<213> ORGANISM: Artificial sequence
<220> FEATURE:
<223> OTHER INFORMATION: Synthetic

<400> SEQUENCE: 32
gccatgagac g 11

<210> SEQ ID NO 33
<211> LENGTH: 11
<212> TYPE: DNA
<213> ORGANISM: Artificial sequence
<220> FEATURE:
<223> OTHER INFORMATION: Synthetic

<400> SEQUENCE: 33
gcagagctat c 11

<210> SEQ ID NO 34
<211> LENGTH: 11
<212> TYPE: DNA
<213> ORGANISM: Artificial sequence
<220> FEATURE:
<223> OTHER INFORMATION: Synthetic

<400> SEQUENCE: 34
cgtctcgata g 11

<210> SEQ ID NO 35
<211> LENGTH: 11
<212> TYPE: DNA
<213> ORGANISM: Artificial sequence
<220> FEATURE:
<223> OTHER INFORMATION: Synthetic

<400> SEQUENCE: 35
cgtctcgcta t 11

<210> SEQ ID NO 36
<211> LENGTH: 11
<212> TYPE: DNA
<213> ORGANISM: Artificial sequence
<220> FEATURE:

<223> OTHER INFORMATION: Synthetic

<400> SEQUENCE: 36
atagcgagac g 11

<210> SEQ ID NO 37
<211> LENGTH: 11
<212> TYPE: DNA
<213> ORGANISM: Artificial sequence
<220> FEATURE:
<223> OTHER INFORMATION: Synthetic

<400> SEQUENCE: 37
aacgagagac g 11

<210> SEQ ID NO 38
<211> LENGTH: 11
<212> TYPE: DNA
<213> ORGANISM: Artificial sequence
<220> FEATURE:
<223> OTHER INFORMATION: Synthetic

<400> SEQUENCE: 38
cgtctctcgt t 11

<210> SEQ ID NO 39
<211> LENGTH: 11
<212> TYPE: DNA
<213> ORGANISM: Artificial sequence
<220> FEATURE:
<223> OTHER INFORMATION: Synthetic

<400> SEQUENCE: 39
cgtctccagg g 11

<210> SEQ ID NO 40
<211> LENGTH: 11
<212> TYPE: DNA
<213> ORGANISM: Artificial sequence
<220> FEATURE:
<223> OTHER INFORMATION: Synthetic

<400> SEQUENCE: 40
ccctggagac g 11

<210> SEQ ID NO 41
<211> LENGTH: 11
<212> TYPE: DNA
<213> ORGANISM: Artificial sequence
<220> FEATURE:
<223> OTHER INFORMATION: Synthetic

<400> SEQUENCE: 41
cgttggagac g 11

<210> SEQ ID NO 42
<211> LENGTH: 11
<212> TYPE: DNA
<213> ORGANISM: Artificial sequence
<220> FEATURE:
<223> OTHER INFORMATION: Synthetic

<400> SEQUENCE: 42
cgtctccaac g 11

<210> SEQ ID NO 43
<211> LENGTH: 11
<212> TYPE: DNA
<213> ORGANISM: Artificial sequence
<220> FEATURE:
<223> OTHER INFORMATION: Synthetic

<400> SEQUENCE: 43
ggtctcgcta t 11

<210> SEQ ID NO 44
<211> LENGTH: 11
<212> TYPE: DNA
<213> ORGANISM: Artificial sequence
<220> FEATURE:
<223> OTHER INFORMATION: Synthetic

<400> SEQUENCE: 44
atagcgagac c 11

<210> SEQ ID NO 45
<211> LENGTH: 11
<212> TYPE: DNA
<213> ORGANISM: Artificial sequence
<220> FEATURE:
<223> OTHER INFORMATION: Synthetic

<400> SEQUENCE: 45
catgggagac c 11

<210> SEQ ID NO 46
<211> LENGTH: 11
<212> TYPE: DNA
<213> ORGANISM: Artificial sequence
<220> FEATURE:
<223> OTHER INFORMATION: Synthetic

<400> SEQUENCE: 46
ggtctcccat g 11

<210> SEQ ID NO 47
<211> LENGTH: 11
<212> TYPE: DNA
<213> ORGANISM: Artificial sequence
<220> FEATURE:
<223> OTHER INFORMATION: Synthetic

<400> SEQUENCE: 47
ggtctcgcat g 11

<210> SEQ ID NO 48
<211> LENGTH: 11
<212> TYPE: DNA
<213> ORGANISM: Artificial sequence
<220> FEATURE:
<223> OTHER INFORMATION: Synthetic

<400> SEQUENCE: 48
catgcgagac c 11

<210> SEQ ID NO 49
<211> LENGTH: 11
<212> TYPE: DNA
<213> ORGANISM: Artificial sequence
<220> FEATURE:
<223> OTHER INFORMATION: Synthetic

<400> SEQUENCE: 49
gctcagagac c 11

<210> SEQ ID NO 50
<211> LENGTH: 11
<212> TYPE: DNA
<213> ORGANISM: Artificial sequence
<220> FEATURE:
<223> OTHER INFORMATION: Synthetic

<400> SEQUENCE: 50
ggtctctgag c 11

<210> SEQ ID NO 51
<211> LENGTH: 11
<212> TYPE: DNA
<213> ORGANISM: Artificial sequence
<220> FEATURE:
<223> OTHER INFORMATION: Synthetic

<400> SEQUENCE: 51
ggtctcgcat g 11

<210> SEQ ID NO 52
<211> LENGTH: 11
<212> TYPE: DNA
<213> ORGANISM: Artificial sequence
<220> FEATURE:
<223> OTHER INFORMATION: Synthetic

<400> SEQUENCE: 52
catgcgagac c 11

<210> SEQ ID NO 53
<211> LENGTH: 11
<212> TYPE: DNA
<213> ORGANISM: Artificial sequence
<220> FEATURE:
<223> OTHER INFORMATION: Synthetic

<400> SEQUENCE: 53
gctcagagac c 11

<210> SEQ ID NO 54
<211> LENGTH: 11
<212> TYPE: DNA
<213> ORGANISM: Artificial sequence
<220> FEATURE:
<223> OTHER INFORMATION: Synthetic

<400> SEQUENCE: 54
ggtctctgag c 11

<210> SEQ ID NO 55
<211> LENGTH: 11
<212> TYPE: DNA
<213> ORGANISM: Artificial sequence
<220> FEATURE:
<223> OTHER INFORMATION: Synthetic

<400> SEQUENCE: 55
ggtctccgct c 11

<210> SEQ ID NO 56
<211> LENGTH: 11

<212> TYPE: DNA
<213> ORGANISM: Artificial sequence
<220> FEATURE:
<223> OTHER INFORMATION: Synthetic

<400> SEQUENCE: 56
gagccgagac c 11

<210> SEQ ID NO 57
<211> LENGTH: 11
<212> TYPE: DNA
<213> ORGANISM: Artificial sequence
<220> FEATURE:
<223> OTHER INFORMATION: Synthetic

<400> SEQUENCE: 57
ggcgggagac c 11

<210> SEQ ID NO 58
<211> LENGTH: 11
<212> TYPE: DNA
<213> ORGANISM: Artificial sequence
<220> FEATURE:
<223> OTHER INFORMATION: Synthetic

<400> SEQUENCE: 58
ggtctcccgc c 11

<210> SEQ ID NO 59
<211> LENGTH: 11
<212> TYPE: DNA
<213> ORGANISM: Artificial sequence
<220> FEATURE:
<223> OTHER INFORMATION: Synthetic

<400> SEQUENCE: 59
ggtctcgata g 11

<210> SEQ ID NO 60
<211> LENGTH: 11
<212> TYPE: DNA
<213> ORGANISM: Artificial sequence
<220> FEATURE:
<223> OTHER INFORMATION: Synthetic

<400> SEQUENCE: 60
ctatcgagac c 11

<210> SEQ ID NO 61
<211> LENGTH: 11
<212> TYPE: DNA
<213> ORGANISM: Artificial sequence
<220> FEATURE:
<223> OTHER INFORMATION: Synthetic

<400> SEQUENCE: 61
cgccagagac c 11

<210> SEQ ID NO 62
<211> LENGTH: 11
<212> TYPE: DNA
<213> ORGANISM: Artificial sequence
<220> FEATURE:
<223> OTHER INFORMATION: Synthetic

<400> SEQUENCE: 62
catgggagac c 11

<210> SEQ ID NO 63
<211> LENGTH: 11
<212> TYPE: DNA
<213> ORGANISM: Artificial sequence
<220> FEATURE:
<223> OTHER INFORMATION: Synthetic

<400> SEQUENCE: 63
ggtctcccat g 11

<210> SEQ ID NO 64
<211> LENGTH: 11
<212> TYPE: DNA
<213> ORGANISM: Artificial sequence
<220> FEATURE:
<223> OTHER INFORMATION: Synthetic

<400> SEQUENCE: 64
ggtctcccat g 11

<210> SEQ ID NO 65
<211> LENGTH: 11
<212> TYPE: DNA
<213> ORGANISM: Artificial sequence
<220> FEATURE:
<223> OTHER INFORMATION: Synthetic

<400> SEQUENCE: 65
catgggagac c 11

<210> SEQ ID NO 66
<211> LENGTH: 11
<212> TYPE: DNA
<213> ORGANISM: Artificial sequence
<220> FEATURE:
<223> OTHER INFORMATION: Synthetic

<400> SEQUENCE: 66
ggaccgagac c 11

<210> SEQ ID NO 67
<211> LENGTH: 11
<212> TYPE: DNA
<213> ORGANISM: Artificial sequence
<220> FEATURE:
<223> OTHER INFORMATION: Synthetic

<400> SEQUENCE: 67
ggtctcggtc c 11

<210> SEQ ID NO 68
<211> LENGTH: 11
<212> TYPE: DNA
<213> ORGANISM: Artificial sequence
<220> FEATURE:
<223> OTHER INFORMATION: Synthetic

<400> SEQUENCE: 68
ggtctcagga c 11

<210> SEQ ID NO 69
<211> LENGTH: 11
<212> TYPE: DNA
<213> ORGANISM: Artificial sequence
<220> FEATURE:
<223> OTHER INFORMATION: Synthetic

<400> SEQUENCE: 69
gtcctgagac c 11

<210> SEQ ID NO 70
<211> LENGTH: 11
<212> TYPE: DNA
<213> ORGANISM: Artificial sequence
<220> FEATURE:
<223> OTHER INFORMATION: Synthetic

<400> SEQUENCE: 70
ccagggagac c 11

<210> SEQ ID NO 71
<211> LENGTH: 11
<212> TYPE: DNA
<213> ORGANISM: Artificial sequence
<220> FEATURE:
<223> OTHER INFORMATION: Synthetic

<400> SEQUENCE: 71
ggtctccctg g 11

<210> SEQ ID NO 72
<211> LENGTH: 11
<212> TYPE: DNA
<213> ORGANISM: Artificial sequence
<220> FEATURE:
<223> OTHER INFORMATION: Synthetic

<400> SEQUENCE: 72
ggtctcgcca g 11

<210> SEQ ID NO 73
<211> LENGTH: 11
<212> TYPE: DNA
<213> ORGANISM: Artificial sequence
<220> FEATURE:
<223> OTHER INFORMATION: Synthetic

<400> SEQUENCE: 73
ctggcgagac c 11

<210> SEQ ID NO 74
<211> LENGTH: 11
<212> TYPE: DNA
<213> ORGANISM: Artificial sequence
<220> FEATURE:
<223> OTHER INFORMATION: Synthetic

<400> SEQUENCE: 74
tgttggagac c 11

<210> SEQ ID NO 75
<211> LENGTH: 11
<212> TYPE: DNA
<213> ORGANISM: Artificial sequence
<220> FEATURE:
<223> OTHER INFORMATION: Synthetic

<400> SEQUENCE: 75
ggtctccaac a 11

<210> SEQ ID NO 76
<211> LENGTH: 11
<212> TYPE: DNA
<213> ORGANISM: Artificial sequence
<220> FEATURE:
<223> OTHER INFORMATION: Synthetic

<400> SEQUENCE: 76
gtcctgagac c 11

<210> SEQ ID NO 77
<211> LENGTH: 11
<212> TYPE: DNA
<213> ORGANISM: Artificial sequence
<220> FEATURE:
<223> OTHER INFORMATION: Synthetic

<400> SEQUENCE: 77
ggtctcagga c 11

<210> SEQ ID NO 78
<211> LENGTH: 11
<212> TYPE: DNA
<213> ORGANISM: Artificial sequence
<220> FEATURE:
<223> OTHER INFORMATION: Synthetic

<400> SEQUENCE: 78
ctggcgagac c 11

<210> SEQ ID NO 79
<211> LENGTH: 11
<212> TYPE: DNA
<213> ORGANISM: Artificial sequence
<220> FEATURE:
<223> OTHER INFORMATION: Synthetic

<400> SEQUENCE: 79
ggtctcgcca g 11

<210> SEQ ID NO 80
<211> LENGTH: 11
<212> TYPE: DNA
<213> ORGANISM: Artificial sequence
<220> FEATURE:
<223> OTHER INFORMATION: Synthetic

<400> SEQUENCE: 80
aacaggagac c 11

<210> SEQ ID NO 81
<211> LENGTH: 11
<212> TYPE: DNA
<213> ORGANISM: Artificial sequence
<220> FEATURE:
<223> OTHER INFORMATION: Synthetic

<400> SEQUENCE: 81
ggtctcctgt t 11

<210> SEQ ID NO 82
<211> LENGTH: 20
<212> TYPE: DNA
<213> ORGANISM: Artificial sequence
<220> FEATURE:
<223> OTHER INFORMATION: Synthetic

<400> SEQUENCE: 82
ttggcgtcgg caaacagtgg 20

<210> SEQ ID NO 83
<211> LENGTH: 20
<212> TYPE: DNA
<213> ORGANISM: Artificial sequence
<220> FEATURE:
<223> OTHER INFORMATION: Synthetic

<400> SEQUENCE: 83
ggcgacgagg tggtcgttgg 20

<210> SEQ ID NO 84
<211> LENGTH: 18
<212> TYPE: DNA
<213> ORGANISM: Artificial sequence
<220> FEATURE:
<223> OTHER INFORMATION: Synthetic

<400> SEQUENCE: 84
accgcaatgg aggcagtg 18

<210> SEQ ID NO 85
<211> LENGTH: 17
<212> TYPE: DNA
<213> ORGANISM: Artificial sequence
<220> FEATURE:
<223> OTHER INFORMATION: Synthetic

<400> SEQUENCE: 85
cgtgcggcaa tcccttt 17

<210> SEQ ID NO 86
<211> LENGTH: 18
<212> TYPE: DNA
<213> ORGANISM: Artificial sequence
<220> FEATURE:
<223> OTHER INFORMATION: Synthetic

<400> SEQUENCE: 86
ctcacacccg atcaggtc 18

<210> SEQ ID NO 87
<211> LENGTH: 20
<212> TYPE: DNA
<213> ORGANISM: Artificial sequence
<220> FEATURE:
<223> OTHER INFORMATION: Synthetic

<400> SEQUENCE: 87
attacgcccc ctttacgagc 20

<210> SEQ ID NO 88
<211> LENGTH: 23
<212> TYPE: DNA
<213> ORGANISM: Artificial sequence
<220> FEATURE:
<223> OTHER INFORMATION: Synthetic

<400> SEQUENCE: 88
agctagctac aaactcaaga gca 23

<210> SEQ ID NO 89

<211> LENGTH: 20
<212> TYPE: DNA
<213> ORGANISM: Artificial sequence
<220> FEATURE:
<223> OTHER INFORMATION: Synthetic

<400> SEQUENCE: 89
taatacgact cactataggg 20

<210> SEQ ID NO 90
<211> LENGTH: 65
<212> TYPE: DNA
<213> ORGANISM: Artificial sequence
<220> FEATURE:
<223> OTHER INFORMATION: Synthetic

<400> SEQUENCE: 90
cgttattatc gcatctgtgc acggatcgag actcaagaca cccgcgctgc ccatccagcc 60
cgaga 65

<210> SEQ ID NO 91
<211> LENGTH: 65
<212> TYPE: DNA
<213> ORGANISM: Artificial sequence
<220> FEATURE:
<223> OTHER INFORMATION: Synthetic

<400> SEQUENCE: 91
cgttattatc gcatctgtgc acggatcgag actcaagaca cccgcgctgc ccatccagcc 60
cgaga 65

<210> SEQ ID NO 92
<211> LENGTH: 58
<212> TYPE: DNA
<213> ORGANISM: Artificial sequence
<220> FEATURE:
<223> OTHER INFORMATION: Synthetic

<400> SEQUENCE: 92
cgttattatc gcatctgtgc acggatcgag acacccgcgc tgcccatcca gcccgaga 58

<210> SEQ ID NO 93
<211> LENGTH: 56
<212> TYPE: DNA
<213> ORGANISM: Artificial sequence
<220> FEATURE:
<223> OTHER INFORMATION: Synthetic

<400> SEQUENCE: 93
cgttattatc gcatctgtgc acggatcgac acccgcgctg cccatccagc ccgaga 56

<210> SEQ ID NO 94
<211> LENGTH: 58
<212> TYPE: DNA
<213> ORGANISM: Artificial sequence
<220> FEATURE:
<223> OTHER INFORMATION: Synthetic

<400> SEQUENCE: 94
cgttattatc gcatctgtgc acggatcgag acacccgcgc tgcccatcca gcccgaga 58

<210> SEQ ID NO 95
<211> LENGTH: 58
<212> TYPE: DNA
<213> ORGANISM: Artificial sequence
<220> FEATURE:
<223> OTHER INFORMATION: Synthetic

<400> SEQUENCE: 95
cgttattatc gcatctgtgc acggatcaag acacccgcgc tgcccatcca gcccgaga 58

<210> SEQ ID NO 96
<211> LENGTH: 58
<212> TYPE: DNA
<213> ORGANISM: Artificial sequence
<220> FEATURE:
<223> OTHER INFORMATION: Synthetic

<400> SEQUENCE: 96
cgttattatc gcatctgtgc acggatcgag acacccgcgc tgcccatcca gcccgaga 58

<210> SEQ ID NO 97
<211> LENGTH: 59
<212> TYPE: DNA
<213> ORGANISM: Artificial sequence
<220> FEATURE:
<223> OTHER INFORMATION: Synthetic

<400> SEQUENCE: 97
cgttattatc gcatctgtgc acggatcgag cacacccgcg ctgcccatcc agcccgaga 59

<210> SEQ ID NO 98
<211> LENGTH: 63
<212> TYPE: DNA
<213> ORGANISM: Artificial sequence
<220> FEATURE:
<223> OTHER INFORMATION: Synthetic

<400> SEQUENCE: 98
cgttattatc gcatctgtgc acggatcgag actagacacc cgcgctgccc atccagcccg 60
aga 63

<210> SEQ ID NO 99
<211> LENGTH: 55
<212> TYPE: DNA
<213> ORGANISM: Artificial sequence
<220> FEATURE:
<223> OTHER INFORMATION: Synthetic

<400> SEQUENCE: 99
cgttattatc gcatctgtgc acggaagaca cccgcgctgc ccatccagcc cgaga 55

<210> SEQ ID NO 100
<211> LENGTH: 56
<212> TYPE: DNA
<213> ORGANISM: Artificial sequence
<220> FEATURE:
<223> OTHER INFORMATION: Synthetic

<400> SEQUENCE: 100
cgttattatc gcatctgtgc acggaaagac acccgcgctg cccatccagc ccgaga 56

<210> SEQ ID NO 101
<211> LENGTH: 58
<212> TYPE: DNA
<213> ORGANISM: Artificial sequence
<220> FEATURE:
<223> OTHER INFORMATION: Synthetic

<400> SEQUENCE: 101

```
cgttattatc gcatctgtgc acggatcgag acacccgcgc tgcccatcca gcccgaga       58


<210> SEQ ID NO 102
<211> LENGTH: 56
<212> TYPE: DNA
<213> ORGANISM: Artificial sequence
<220> FEATURE:
<223> OTHER INFORMATION: Synthetic

<400> SEQUENCE: 102

cgttattatc gcatctgtgc acggatagac acccgcgctg cccatccagc ccgaga         56


<210> SEQ ID NO 103
<211> LENGTH: 58
<212> TYPE: DNA
<213> ORGANISM: Artificial sequence
<220> FEATURE:
<223> OTHER INFORMATION: Synthetic

<400> SEQUENCE: 103

cgttattatc gcatctgtgc acggatcgag acacccgcgc tgcccatcca gcccgaga       58


<210> SEQ ID NO 104
<211> LENGTH: 58
<212> TYPE: DNA
<213> ORGANISM: Artificial sequence
<220> FEATURE:
<223> OTHER INFORMATION: Synthetic

<400> SEQUENCE: 104

cgttattatc gcatctgtgc acggatcgag acacccgcgc tgcccatcca gcccgaga       58


<210> SEQ ID NO 105
<211> LENGTH: 52
<212> TYPE: DNA
<213> ORGANISM: Artificial sequence
<220> FEATURE:
<223> OTHER INFORMATION: Synthetic

<400> SEQUENCE: 105

cgttattatc gcatctgtgc acggacaccc gcgctgccca tccagcccga ga             52


<210> SEQ ID NO 106
<211> LENGTH: 58
<212> TYPE: DNA
<213> ORGANISM: Artificial sequence
<220> FEATURE:
<223> OTHER INFORMATION: Synthetic

<400> SEQUENCE: 106

cgttattatc gcatctgtgc acggatcgag acacccgcgc tgcccatcca gcccgaga       58


<210> SEQ ID NO 107
<211> LENGTH: 58
<212> TYPE: DNA
<213> ORGANISM: Artificial sequence
<220> FEATURE:
<223> OTHER INFORMATION: Synthetic

<400> SEQUENCE: 107

cgttattatc gcatctgtgc acggatcgag acacccgcgc tgcccatcca gcccgaga       58


<210> SEQ ID NO 108
<211> LENGTH: 56
<212> TYPE: DNA
<213> ORGANISM: Artificial sequence
```

<220> FEATURE:
<223> OTHER INFORMATION: Synthetic

<400> SEQUENCE: 108
cgttattatc gcatctgtgc acggatcgac acccgcgctg cccacccagc ccgaga 56

<210> SEQ ID NO 109
<211> LENGTH: 55
<212> TYPE: DNA
<213> ORGANISM: Artificial sequence
<220> FEATURE:
<223> OTHER INFORMATION: Synthetic

<400> SEQUENCE: 109
cgttattatc gcatctgtgc acggaagaca cccgcgctgc ccatccagcc cgaga 55

<210> SEQ ID NO 110
<211> LENGTH: 58
<212> TYPE: DNA
<213> ORGANISM: Artificial sequence
<220> FEATURE:
<223> OTHER INFORMATION: Synthetic

<400> SEQUENCE: 110
cgttattatc gcatctgtgc acggatcgag acacccgcgc tgcccatcca gcccgaga 58

<210> SEQ ID NO 111
<211> LENGTH: 40
<212> TYPE: DNA
<213> ORGANISM: Artificial sequence
<220> FEATURE:
<223> OTHER INFORMATION: Synthetic

<400> SEQUENCE: 111
cgttattatc gcatctgtgc acggcccatc cagcccgaga 40

<210> SEQ ID NO 112
<211> LENGTH: 58
<212> TYPE: DNA
<213> ORGANISM: Artificial sequence
<220> FEATURE:
<223> OTHER INFORMATION: Synthetic

<400> SEQUENCE: 112
cgttattatc gcatctgtgc acggatcgag acacccgcgc tgcccatcca gcccgaga 58

<210> SEQ ID NO 113
<211> LENGTH: 58
<212> TYPE: DNA
<213> ORGANISM: Artificial sequence
<220> FEATURE:
<223> OTHER INFORMATION: Synthetic

<400> SEQUENCE: 113
cgttattatc gcatctgtgc acggatcgag acacccgcgc tgcccatcca gcccgaga 58

<210> SEQ ID NO 114
<211> LENGTH: 56
<212> TYPE: DNA
<213> ORGANISM: Artificial sequence
<220> FEATURE:
<223> OTHER INFORMATION: Synthetic

<400> SEQUENCE: 114
cgttattatc gcatctgtgc acggatcgac acccgcgctg cccacccagc ccgaga 56

<210> SEQ ID NO 115
<211> LENGTH: 56
<212> TYPE: DNA
<213> ORGANISM: Artificial sequence
<220> FEATURE:
<223> OTHER INFORMATION: Synthetic

<400> SEQUENCE: 115
cgttattatc gcatctgtgc acggatagac acccgcgctg cccatccagc ccgaga 56

<210> SEQ ID NO 116
<211> LENGTH: 58
<212> TYPE: DNA
<213> ORGANISM: Artificial sequence
<220> FEATURE:
<223> OTHER INFORMATION: Synthetic

<400> SEQUENCE: 116
cgttattatc gcatctgtgc acggatcgag acacccgcgc tgcccatcca gcccgaga 58

<210> SEQ ID NO 117
<211> LENGTH: 58
<212> TYPE: DNA
<213> ORGANISM: Artificial sequence
<220> FEATURE:
<223> OTHER INFORMATION: Synthetic

<400> SEQUENCE: 117
cgttattatc gcatctgtgc acggatcgag acacccgcgc tgcccatcca gcccgaga 58

<210> SEQ ID NO 118
<211> LENGTH: 58
<212> TYPE: DNA
<213> ORGANISM: Artificial sequence
<220> FEATURE:
<223> OTHER INFORMATION: Synthetic

<400> SEQUENCE: 118
cgttattatc gcatctgtgc acggatcgag acacccgcgc tgcccatcca gcccgaga 58

<210> SEQ ID NO 119
<211> LENGTH: 39
<212> TYPE: DNA
<213> ORGANISM: Artificial sequence
<220> FEATURE:
<223> OTHER INFORMATION: Synthetic

<400> SEQUENCE: 119
tattcagacg tcaggatgct ccggtgtaat tcagatttt 39

<210> SEQ ID NO 120
<211> LENGTH: 40
<212> TYPE: DNA
<213> ORGANISM: Artificial sequence
<220> FEATURE:
<223> OTHER INFORMATION: Synthetic

<400> SEQUENCE: 120
cgcatctgtg cacggatcga gacacccgcg ctgcccatcc 40

<210> SEQ ID NO 121
<211> LENGTH: 35
<212> TYPE: DNA
<213> ORGANISM: Artificial sequence
<220> FEATURE:
<223> OTHER INFORMATION: Synthetic

```
<400> SEQUENCE: 121

ttgggaacaa gatggcggtg attttctgtt ggcaa                             35


<210> SEQ ID NO 122
<211> LENGTH: 36
<212> TYPE: DNA
<213> ORGANISM: Artificial sequence
<220> FEATURE:
<223> OTHER INFORMATION: Synthetic

<400> SEQUENCE: 122

ggtacgacag gttcagcctt aaagcctgag cctggt                            36


<210> SEQ ID NO 123
<211> LENGTH: 36
<212> TYPE: DNA
<213> ORGANISM: Artificial sequence
<220> FEATURE:
<223> OTHER INFORMATION: Synthetic

<400> SEQUENCE: 123

tgtgatccct taccgatgtg atctcatgta cctcag                            36


<210> SEQ ID NO 124
<211> LENGTH: 35
<212> TYPE: DNA
<213> ORGANISM: Artificial sequence
<220> FEATURE:
<223> OTHER INFORMATION: Synthetic

<400> SEQUENCE: 124

gtcaggacat ctcaactcca gaggagcata ttaag                             35
```